(12) United States Patent
Tada et al.

(10) Patent No.: US 12,048,413 B2
(45) Date of Patent: Jul. 30, 2024

(54) DIAGNOSTIC ASSISTANCE METHOD, DIAGNOSTIC ASSISTANCE SYSTEM, DIAGNOSTIC ASSISTANCE PROGRAM, AND COMPUTER-READABLE RECORDING MEDIUM STORING THEREIN DIAGNOSTIC ASSISTANCE PROGRAM FOR DISEASE BASED ON ENDOSCOPIC IMAGE OF DIGESTIVE ORGAN

(71) Applicant: AI MEDICAL SERVICE INC., Tokyo (JP)

(72) Inventors: Tomohiro Tada, Tokyo (JP); Hiroaki Saito, Tokyo (JP); Satoki Shichijyo, Tokyo (JP); Yuma Endo, Tokyo (JP); Kazuharu Aoyama, Tokyo (JP); Atsuo Yamada, Tokyo (JP); Kentaro Nakagawa, Tokyo (JP); Ryu Ishihara, Tokyo (JP); Syuntaro Inoue, Tokyo (JP)

(73) Assignee: AI MEDICAL SERVICE INC., Tokyo (JP)

( * ) Notice: Subject to any disclaimer, the term of this patent is extended or adjusted under 35 U.S.C. 154(b) by 809 days.

(21) Appl. No.: 17/252,877

(22) PCT Filed: Jun. 20, 2019

(86) PCT No.: PCT/JP2019/024613
§ 371 (c)(1),
(2) Date: Dec. 16, 2020

(87) PCT Pub. No.: WO2019/245009
PCT Pub. Date: Dec. 26, 2019

(65) Prior Publication Data
US 2021/0153808 A1    May 27, 2021

(30) Foreign Application Priority Data

Jun. 22, 2018  (JP) .................................. 2018-119381
Jul. 13, 2018  (JP) .................................. 2018-133760
(Continued)

(51) Int. Cl.
*G06T 7/00*    (2017.01)
*A61B 1/00*    (2006.01)
(Continued)

(52) U.S. Cl.
CPC .... *A61B 1/00009* (2013.01); *A61B 1/000096* (2022.02); *A61B 1/00016* (2013.01);
(Continued)

(58) Field of Classification Search
None
See application file for complete search history.

(56) References Cited

U.S. PATENT DOCUMENTS 10,255,679 B2*  4/2019  Yin ......................... G06F 18/22
2003/0220549 A1* 11/2003  Liu ...................... A61B 5/0059
                                                    600/317
(Continued)

FOREIGN PATENT DOCUMENTS

CN    107705852 A    2/2018
JP    2006218138 A    8/2006
(Continued)

OTHER PUBLICATIONS

Anwar et al., Medical Image Analysis using Convolutional Neural Networks: A Review, Journal of Medical Systems (Year: 2018).*
(Continued)

*Primary Examiner* — Mohammed Rachedine
(74) *Attorney, Agent, or Firm* — Maier & Maier, PLLC

(57) ABSTRACT

A diagnostic assistance method for a disease based on an endoscopic image of a digestive organ with use of a con-
(Continued)

volutional neural network (CNN). A diagnostic assistance method for a disease based on an endoscopic image of a digestive organ with a CNN trains the CNN using a first endoscopic image of the digestive organ and at least one final diagnosis result on positivity or negativity to the disease in the digestive organ, a past disease, a severity level, and information corresponding to a site where an image is captured, the final diagnosis result corresponding to the first endoscopic image, and the trained CNN outputs at least one of a probability of the positivity and/or the negativity to the disease, a probability of the past disease, a severity level of the disease, an invasion depth of the disease, and a probability corresponding to the site where the image is captured.

31 Claims, 12 Drawing Sheets

(30) Foreign Application Priority Data

Nov. 21, 2018 (JP) .................................. 2018-218490
Feb. 25, 2019 (JP) .................................. 2019-032163

(51) Int. Cl.
| | |
|---|---|
| A61B 1/04 | (2006.01) |
| A61B 1/273 | (2006.01) |
| A61B 1/31 | (2006.01) |
| A61B 5/00 | (2006.01) |
| A61B 6/03 | (2006.01) |
| A61B 8/13 | (2006.01) |
| G06N 3/04 | (2023.01) |
| G06N 3/08 | (2023.01) |
| G16H 30/00 | (2018.01) |
| G16H 30/20 | (2018.01) |
| G16H 30/40 | (2018.01) |
| G16H 40/67 | (2018.01) |
| G16H 50/20 | (2018.01) |
| G16H 50/30 | (2018.01) |
| G16H 70/60 | (2018.01) |

(52) U.S. Cl.
CPC .......... *A61B 1/00045* (2013.01); *A61B 1/041* (2013.01); *A61B 5/0022* (2013.01); *A61B 5/0035* (2013.01); *A61B 5/4233* (2013.01); *A61B 5/4238* (2013.01); *A61B 5/4255* (2013.01); *A61B 5/7267* (2013.01); *A61B 6/032* (2013.01); *A61B 8/13* (2013.01); *G06N 3/04* (2013.01); *G06N 3/08* (2013.01); *G06T 7/0016* (2013.01); *G16H 30/20* (2018.01); *G16H 30/40* (2018.01); *G16H 40/67* (2018.01); *G16H 50/20* (2018.01); *G16H 50/30* (2018.01); *G16H 70/60* (2018.01); *G06T 2207/10068* (2013.01); *G06T 2207/20081* (2013.01); *G06T 2207/20084* (2013.01); *G06T 2207/30028* (2013.01); *G06T 2207/30092* (2013.01)

(56) References Cited

U.S. PATENT DOCUMENTS

| | | | |
|---|---|---|---|
| 2007/0085686 A1* | 4/2007 | Oz | A61B 1/00016 235/492 |
| 2012/0071710 A1* | 3/2012 | Gazdzinski | A61B 8/12 600/101 |
| 2015/0065803 A1* | 3/2015 | Douglas | G06T 7/143 600/200 |
| 2015/0208901 A1* | 7/2015 | Gazdzinski | G16Z 99/00 600/302 |
| 2017/0084036 A1 | 3/2017 | Pheiffer et al. | |

FOREIGN PATENT DOCUMENTS

| | | | | |
|---|---|---|---|---|
| JP | 2011130793 A | | 7/2011 | |
| WO | WO-2009049038 A1 * | | 4/2009 | ............... A61B 5/06 |
| WO | WO-2010013247 A1 * | | 2/2010 | ......... A61B 1/00147 |
| WO | 2016/185617 A1 | | 11/2016 | |
| WO | 2017/175282 A1 | | 10/2017 | |
| WO | WO-2018074833 A1 * | | 4/2018 | ............... A61B 1/00 |
| WO | WO-2018087298 A1 * | | 5/2018 | ............. A61K 38/28 |
| WO | 2019/088121 A1 | | 5/2019 | |

OTHER PUBLICATIONS

Jia et al. "A Deep Convolutional Neural Network for Bleeding Detection in Wireless Capsule Endoscopy Images." 38th Annual International Conference of the IEEE Engineering in Medicine and Biology Society. IEEE. 2016. ISSN 1558-4615. 5 pages.
Kudo et al. "Can endocytoscopy be a virtual biopsy?" Endoscopia Digestiva (issued in June). vol. 27, Issue 6. Japan. Tokyo Igakusha Ltd. Jun. 25, 2015. ISSN 0915-3217. 6 pages with machine-generated English translation.
Miyazaki. "Using a convolutional neural network Position detection of small intestinal lesions on capsule endoscopy." Information Processing Society of Japan Research Report, IPSJ SIG Technical Report. vol. 126-CVM-202 No. 23. May 12, 2016. 18 pages with machine-generated English translation.
Yamada et al. "Development of a real-time automatic endoscopic image analysis system for detection of colorectal cancer and pre-cancerous lesions using an artificial intelligence system based on morphological information quantification." Journal of Japanese Society of Gastroenterology. vol. 114, an extra issue (competitions). The Japanese Society of Gastroenterology. Sep. 15, 2017. A498. ISSN 0446-6586. 3 pages with machine-generated English translation.
Japanese Office Action issued on Aug. 10, 2021, in connection with corresponding JP Application No. 2019-032163 (11 pp., including machine-generated English translation).
Japanese Office Action issued on Oct. 5, 2021, in connection with corresponding JP Application No. 2020-557614 (18 pp., including machine-generated English translation).
International Search Report issued on Feb. 22, 2021, in connection with corresponding International Application No. PCT/JP2020/035652 (17 pp., including machine-generated English translation).
Bibault, Jean-Emmanuel et al. "Big Data and machine learning in radiation oncology: State of the art and future prospects." Cancer Letters. vol. 382, No. 1. Nov. 1, 2016. 12 pages.
Esteva, Andre et al. "Dermatologist-level classification of skin cancer with deep neural networks." Nature. vol. 542. Feb. 2, 2017. 12 pages.
Gulshan, Varun et al. Development and Validation of a Deep Learning Algorithm for Detection of Diabetic Retinopathy in Retinal Fundus Photographs. JAMA. vol. 316, No. 22. Dec. 13, 2016. 19 pages.
Byrne, Michael F et al. "Real-time differentiation of adenomatous and hyperplastic diminutive colorectal polyps during analysis of unaltered videos of standard colonoscopy using a deep learning model." Gut. vol. 68. 2019. pp. 94-100.
Chen, Peng-Jen et al. "Accurate Classification of Diminutive Colorectal Polyps Using Computer-Aided Analysis." Gastroenterology. vol. 154, No. 3. Feb. 2018. pp. 568-575.
Misawa, Masashi et al. "Artificial Intelligence-Assisted Polyp Detection for Colonoscopy: Initial Experience." Gastroenterology in Motion. vol. 154. 2018. pp. 2027-2029. 6 pages.
Takiyama, Hirotoshi et al. "Automatic anatomical classification of esophagogastroduodenoscsopy images using deep convolutional neural networks." Nature, Scientific Reports. vol. 8. 2018. 8 pages.

(56) References Cited

OTHER PUBLICATIONS

Hirasawa, Toshiaki et al. "Application of artificial intelligence using a convolutional neural network for detecting gastric cancer in endoscopic images." Gastric Cancer. vol. 21. 2018. pp. 653-660.

Shichijo, Staoki et al. "Application of Convolutional Neural Networks in the Diagnosis of Helicobacter pylori Infection Based on Endoscopic Images." EBioMedicine. vol. 25. 2017. pp. 106-111.

Akovidis, Dimitris K et al. "Automatic lesion detection in capsule endoscopy based on color saliency: closer to an essential adjunct for reviewing software." New Methods: Clinical Endoscopy. vol. 80, No. 5. 2014. pp. 877-883.

Farley, Heather A. et al. "Surgical Treatment of Small Bowel Neuroendocrine Tumors." Hematol Oncol Clin N Am. vol. 30. 2016. pp. 49-61.

Karargyris et al., "Wireless Capsule Endoscopy and Endoscopic Imaging: A Survey on Various Methodologies Presented"; IEEE Engineering in Medicine and Biology Magazine; Jan./Feb. 2010; vol. 29, No. 1, pp. 72-83.

Anwar et al., "Medical Image Analysis using Convolutional Neural Networks: A Review"; Journal of Medical Systems; Sep. 4, 2017; pp. 1-20.

Extended European Search Report issued on Jul. 15, 2022, in connection with corresponding European Application No. 19887179.0; 14 pages.

Satoki Shichijo et al., "Application of Convolutional Neural Networks in the Diagnosis of Helicobacter pylori Infection Based onEndoscopic Images", Ebiomedicine, vol. 25, Oct. 14, 2017 (Oct. 14, 2017), pp. 106-111.

Toshiaki Hirasawa et al., "Application of artificial intelligence using a convolutional neural network for detecting gastric cancer in endoscopic images", Gastric Cancer, Springer Singapore, Singapore, vol. 21, No. 4, Jan. 15, 2018 (Jan. 15, 2018), pp. 653-660.

Extended European Search Report issued on Feb. 16, 2022, in connection with corresponding European Application No. 19823151.6; 11 pages.

* cited by examiner

FIG.7
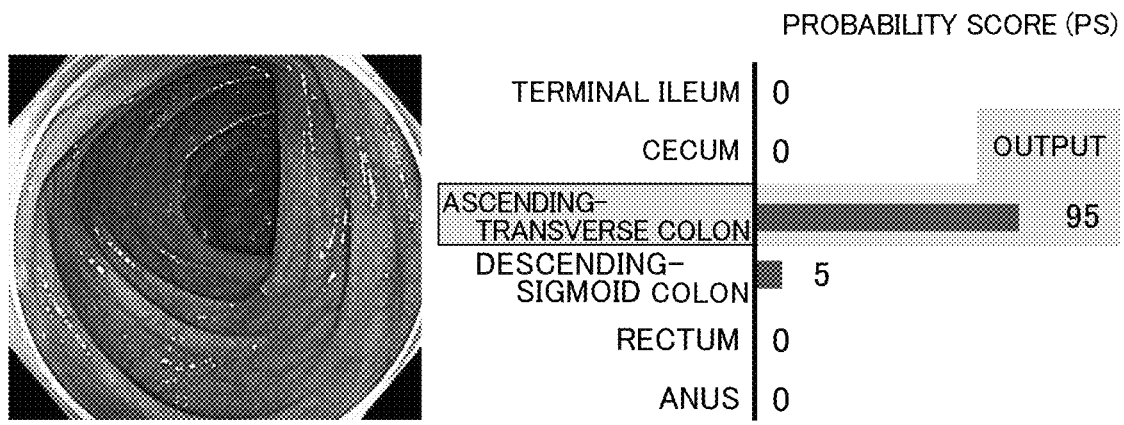
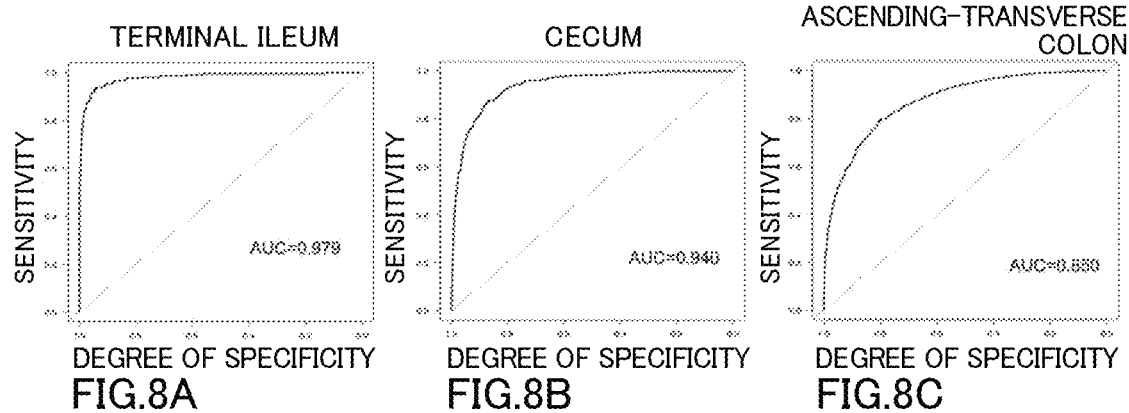
FIG.8A  FIG.8B  FIG.8C
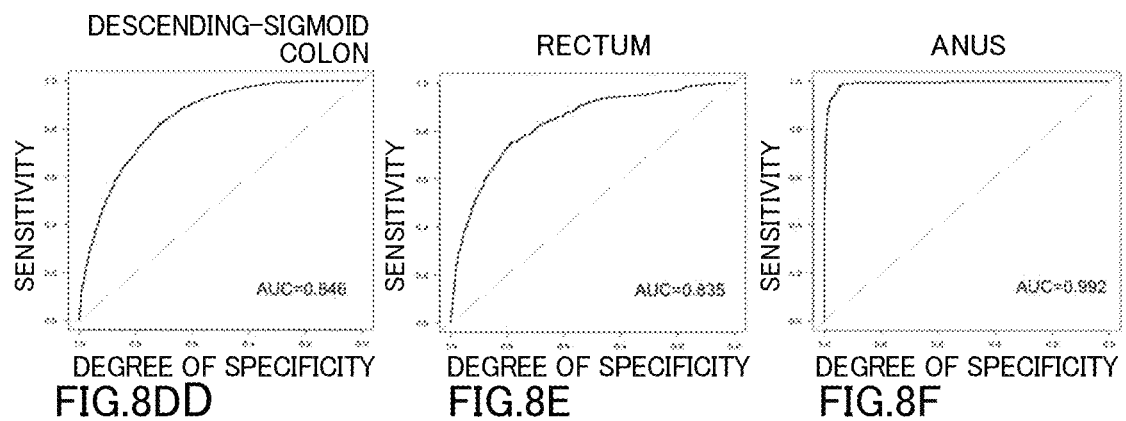
FIG.8DD  FIG.8E  FIG.8F

CORRECT CLASSIFICATION

| | PROBABILITY SCORE (PS) |
|---|---|
| TERMINAL ILEUM | 0 |
| CECUM | 0 |
| ASCENDING-TRANSVERSE COLON | 0 |
| DESCENDING-SIGMOID COLON | 0 |
| RECTUM | 0 |
| ANUS | 100 |

ERRONEOUS CLASSIFICATION

| | PROBABILITY SCORE (PS) |
|---|---|
| TERMINAL ILEUM | 0 |
| CECUM | 0 |
| ASCENDING-TRANSVERSE COLON | 0 |
| DESCENDING-SIGMOID COLON | 0 |
| RECTUM | 0 |
| ANUS | 99 |

FIG.12
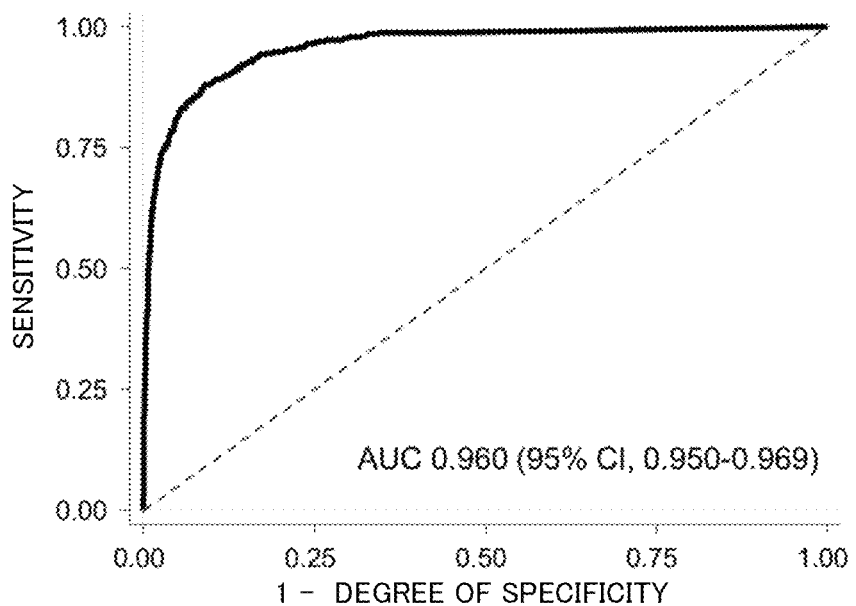
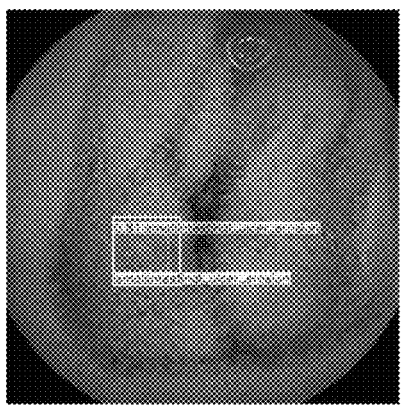
FIG.13A
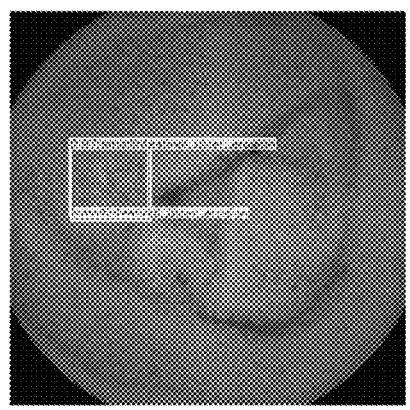
FIG.13B
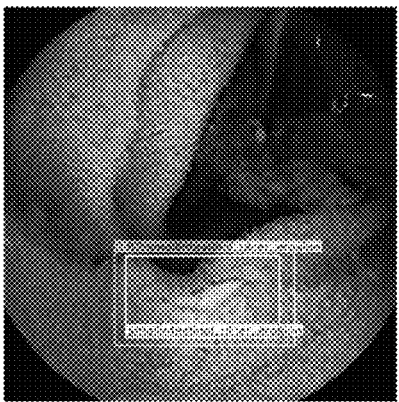
FIG.13C
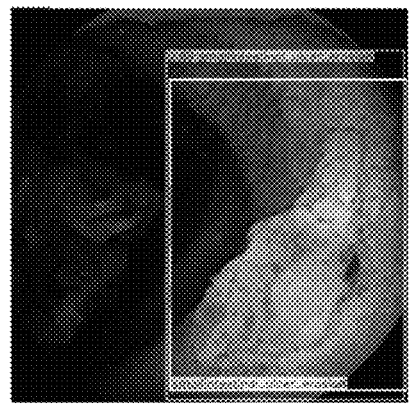
FIG.13D

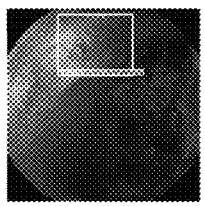
FIG.14A
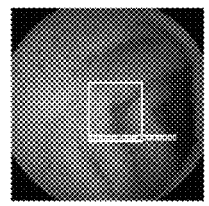
FIG.14B
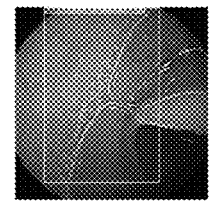
FIG.14C
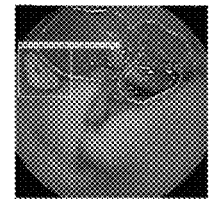
FIG.14D
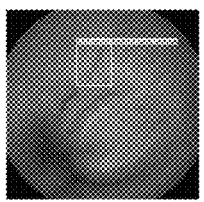
FIG.14E
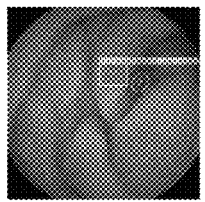
FIG.14F
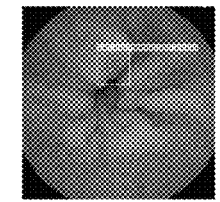
FIG.14G
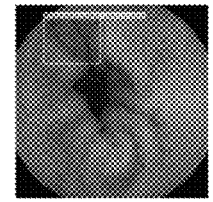
FIG.14H
FIG.15
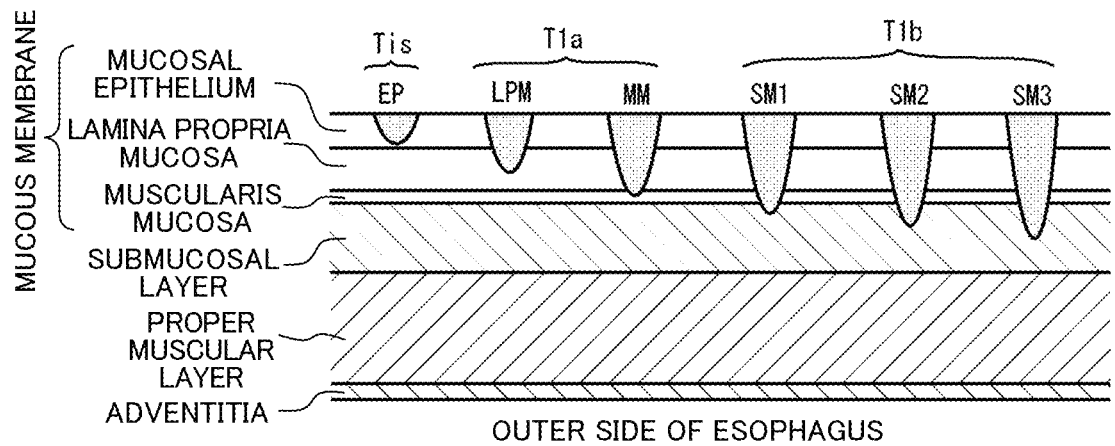
FIG.16
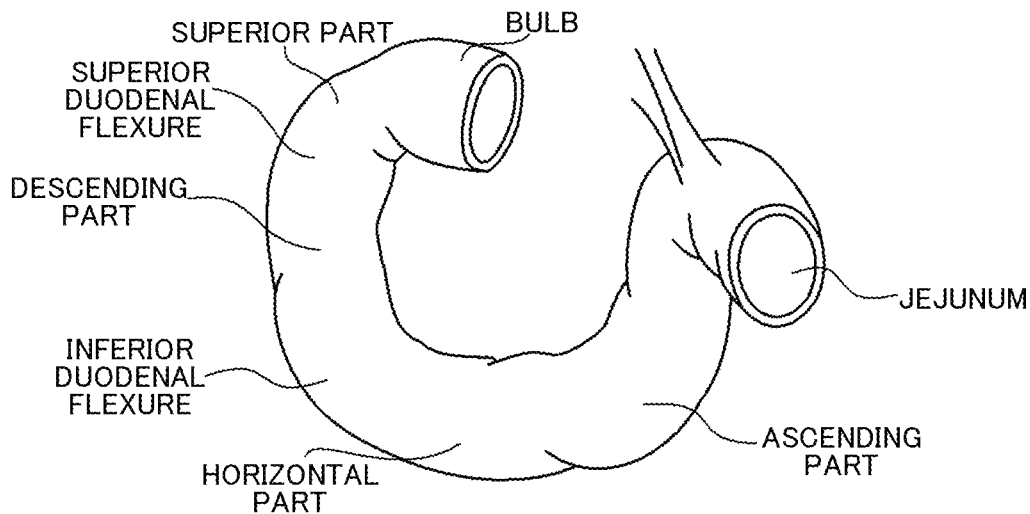

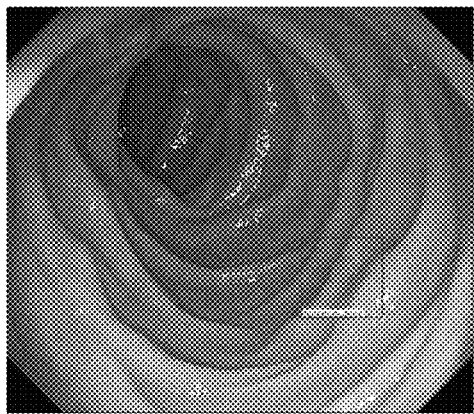 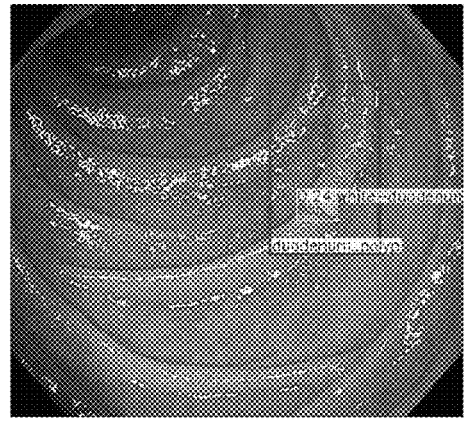
FIG.19A  FIG.19B
FIG.20
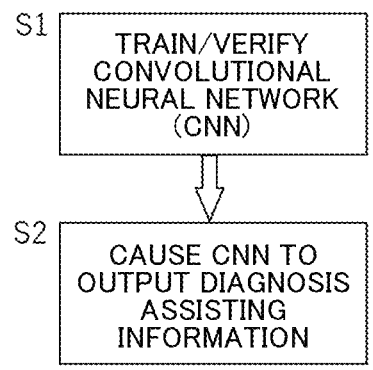
FIG.21
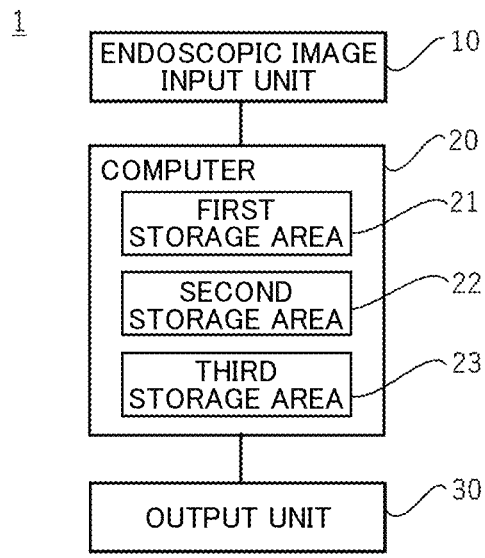

DIAGNOSTIC ASSISTANCE METHOD, DIAGNOSTIC ASSISTANCE SYSTEM, DIAGNOSTIC ASSISTANCE PROGRAM, AND COMPUTER-READABLE RECORDING MEDIUM STORING THEREIN DIAGNOSTIC ASSISTANCE PROGRAM FOR DISEASE BASED ON ENDOSCOPIC IMAGE OF DIGESTIVE ORGAN

FIELD

The present invention relates to a diagnostic assistance method, a diagnostic assistance system, a diagnostic assistance program, and a computer-readable recording medium storing therein the diagnostic assistance program for a disease based on an endoscopic image of a digestive organ with use of a neural network.

BACKGROUND

Many endoscopic examinations of digestive organs, such as the larynx, pharynx, esophagus, stomach, duodenum, biliary tract, pancreatic duct, small bowel, and large bowel, are being performed. Endoscopic examinations of upper digestive organs are often performed for screening of stomach cancers, esophageal cancers, peptic ulcer, and reflux gastritis, for example, and endoscopic examinations of the large bowel are often performed for screening of colorectal cancers, colon polyps, and ulcerative colitis, for example. In particular, endoscopic examinations of the upper digestive organs are effective as specific examinations for various symptoms of an upper abdomen, as detailed examinations in response to positive results from barium examinations of stomach diseases, and as detailed examinations in response to abnormal serum pepsinogen levels, which are generally incorporated in regular health checkups in Japan. Furthermore, stomach cancer screening has recently come to be shifted from conventional barium examinations to gastric endoscopic examinations.

Stomach cancers are one of the most common malignant tumors, and a few years ago it was estimated that there were approximately one million cases of stomach cancers worldwide. Of the root causes of the development of stomach cancers, infection to *Helicobacter pylori* (hereinafter, sometimes referred to as "*H. pylori*") induces atrophic gastritis and intestinal metaplasia, and eventually leads to an onset of a stomach cancer. It is now considered that *H. pylori* contributes to 98% of the cases of noncardia stomach cancers in the world. Patients who have been infected with *H. pylori* have higher risks for stomach cancers. Considering that the incidence of stomach cancers has been reduced by eradicating *H. pylori*, the International Agency for Research on Cancer classifies *H. pylori* as a clear carcinogen. Based on this result, it is useful to eradicate *H. pylori* to reduce the risk of the onset of stomach cancers, and the eradication of *H. pylori* with the use of an antibacterial drug has come to be a treatment covered by the public health insurance system in Japan, and will be a highly recommended treatment in terms of health and hygiene in the future, too. In fact, the Ministry of Health, Labour and Welfare in Japan approved the coverage of eradicating treatment of gastritis caused by *H. pylori* infection by the public health insurance in February 2013.

Gastric endoscopic examinations provide extremely useful information to differential diagnoses of *H. pylori* infections. Clearly visible capillaries (regular arrangement of collecting venules (RAC)) and fundi gland polyposis are characteristic of *H. pylori* negative gastric mucosa. Atrophy, redness, mucosal swelling, and enlarged gastric folds are typical observations found in gastritis caused by *H. pylori* infections. Red patches are characteristic of gastric mucosa after *H. pylori* eradication. Accurate endoscopic diagnoses of *H. pylori* infections are supported by various examinations such as measurement of anti-*H. pylori* IgG level in the blood or the urine, coproantibody measurement, urea breath tests, and rapid urease tests, and patients with the positive examination result can proceed to the *H. pylori* eradication. While endoscopic examinations are widely used in examining gastric lesions, if it is possible also to identify the presence of *H. pylori* infections during the checkups for gastric lesions without the need of clinical specimen analyses, the burden on patients can be reduced, because the patients are not required to go through standardized blood tests, urinalyses, and the like, and a contribution can also be made from the viewpoint of medical economics.

Esophageal cancers are the eighth most common cancer and have the sixth highest cause of death from cancer. In 2012, it was estimated that there were 456,000 new cases and 400,000 deaths. In Europe and North America, the incidence of esophageal adenocarcinoma has been increasing rapidly, and squamous cell carcinoma (SCC) is the most common type of the esophageal cancer, accounting for 80% of cases worldwide. The overall survival rate of the patients with an advanced esophageal SCC has also remained low. However, if this kind of tumor is detected as a mucosal cancer or submucosal cancer, a benign prognosis can be expected.

Furthermore, total colonoscopy (CS) enables detections of colorectal diseases such as colorectal cancers (CRC), colorectal polyps, and inflammatory bowel diseases, at a high sensitivity and a high degree of specificity. Early diagnoses of such diseases enable patients to be treated at an earlier stage for a better prognosis, so that it is important to ensure sufficient CS quality.

Although the endoscopic examinations of the upper digestive organs and the large bowel have come to be widely practiced as described above, endoscopic examinations of the small bowel are not practiced very often because it is difficult to insert a typical endoscope into the small bowel. A typical endoscope has a length of about two meters or so. In order to insert the endoscope into the small bowel, it is necessary to orally insert the endoscope into the small bowel, via the stomach and the duodenum, or through the anus via the large bowel. Furthermore, because the small bowel itself is a long organ with a length of six to seven meters, it is difficult to insert a typical endoscope into the entire small bowel and to make observations. Therefore, for the endoscopic examinations of the small bowel, either double balloon endoscopy (see Patent Literature 1) or wireless capsule endoscopy (hereinafter, sometimes simply referred to as "WCE") (see Patent Literature 2) has been put to use.

Double balloon endoscopy is a method in which a balloon provided at the tip of the endoscope and another balloon provided at the tip of an over-tube covering the endoscope are inflated and deflated alternatingly or simultaneously, and an examination is carried out by reducing the length of, and straightening the long small bowel in a manner hauling the small bowel, but it is difficult to examine the entire length of the small bowel at once, because the length of the small bowel is long. Therefore, examinations of the small bowel by double balloon endoscopy are usually carried out at two separate steps, one through the mouth, and the other through the anus.

WCE endoscopy is carried out by having a patient swallow an orally ingestible capsule that includes a camera, a flash, a battery, a transmitter, and the like, and by causing the capsule to transmit captured images while the capsule is moving through the digestive tract, wirelessly to the external, and by receiving and recording the images externally, so that images of the entire small bowel can be captured all at once.

Generally speaking, small bowel refers to the duodenum, jejunum, and ileum, and a small bowel adenocarcinoma is defined as a duodenal adenocarcinoma, a jejunal adenocarcinoma, or an ileal adenocarcinoma, excluding an ampullary adenocarcinoma (a cancer in the ampulla of Vater). Small bowel adenocarcinoma accounts for less than 0.5% of all malignant tumors in the digestive tract, and accounts for less than 5% of all malignant tumors. The annual incidence of small bowel adenocarcinoma in the Western countries is extremely low, being 2.2 to 5.7 cases per million people, and small bowel adenocarcinoma is considered as a rare cancer. The duodenal adenocarcinoma accounts for 45% of the small bowel adenocarcinoma, and the survival rate over five years is the lowest among the malignant small bowel tumors, and is less than 30%. When the diagnosis is made after the disease has advanced, a highly invasive treatment such as pancreatoduodenectomy resection will be required, and, if it is diagnosed as an irresectable advanced cancer, the prognosis will be bad.

Furthermore, a superficial non-ampullary duodenal epithelial tumor (hereinafter, sometimes referred to as "SNADET") is not formed in the ampulla of Vater, and is defined as a mucosal or submucosal sporadic tumor in the duodenum. This kind of tumors rarely induces metastasis to a lymph node, and a large portion of SNADET cases can be treated using a less invasive treatment, such as endoscopic resection (ER).

PATENT LITERATURE

Patent Literature 1: Japanese Patent Application Laid-open No. 2002-301019
Patent Literature 2: Japanese Patent Application Laid-open No. 2006-095304
Patent Literature 3: Japanese Patent Application Laid-open No. 2017-045341
Patent Literature 4: Japanese Patent Application Laid-open No. 2017-067489

NON PATENT LITERATURE

Non Patent Literature 1: Bibault J E, Giraud P, Burgun A. Big Data and machine learning in radiation oncology: State of the art and future prospects. Cancer Lett. 2016; 382(1):110-117.
Non Patent Literature 2: Esteva A, Kuprel B, Novoa R A, et al. Dermatologist-level classification of skin cancer with deep neural networks. Nature. 2017; 542(7639): 115-118.
Non Patent Literature 3: Gulshan V, Peng L, Coram M, et al. Development and Validation of a Deep Learning Algorithm for Detection of Diabetic Retinopathy in Retinal Fundus Photographs. JAMA. 2016; 316(22): 2402-2410.
Non Patent Literature 4: Byrne M F, Chapados N, Soudan F, et al. Real-time differentiation of adenomatous and hyperplastic diminutive colorectal polyps during analysis of unaltered videos of standard colonoscopy using a deep learning model. Gut. 2017.
Non Patent Literature 5: Chen P J, Lin M C, Lai M J, Lin J C, Lu H H, Tseng V S. Accurate Classification of Diminutive Colorectal Polyps Using Computer-Aided Analysis. Gastroenterology. 2018; 154(3):568-575.
Non Patent Literature 6: Misawa M, Kudo S E, Mori Y, et al. Artificial Intelligence-Assisted Polyp Detection for Colonoscopy: Initial Experience. Gastroenterology. 2018.
Non Patent Literature 7: Takiyama H, Ozawa T, Ishihara S, et al. Automatic anatomical classification of esophagogastroduodenoscopy images using deep convolutional neural networks. Sci Rep. 2018; 8(1):7497.
Non Patent Literature 8: Hirasawa T, Aoyama K, Tanimoto T, et al. Application of artificial intelligence using a convolutional neural network for detecting gastric cancer in endoscopic images. Gastric Cancer. 2018.
Non Patent Literature 9: Shichijo S, Nomura S, Aoyama K, et al. Application of Convolutional Neural Networks in the Diagnosis of *Helicobacter pylori* Infection Based on Endoscopic Images EBioMedicine. 2017; 25:106-111.
Non Patent Literature 10: Iakovidis D K, Koulaouzidis A. Automatic lesion detection in capsule endoscopy based on color saliency: closer to an essential adjunct for reviewing software. Gastrointestinal endoscopy 2014 November; 80(5):877-83.
Non Patent Literature 11: Farley H A, Pommier R F. Surgical Treatment of Small Bowel Neuroendocrine Tumors. Hematology/oncology clinics of North America. 2016; 30(1):49-61.

SUMMARY

In such endoscopic examinations of digestive organs, a large number of endoscopic images are collected, and endoscopy specialists are obliged to double-check the endoscopic images for the purpose of accuracy management. With some tens of thousands of endoscopic health checkups being carried out every year, the number of images to be interpreted by an endoscopy specialist for the secondary interpretation is enormous, e.g., approximately 2800 images per person per hour, and it has been a heavy burden in practice.

In the WCE examinations of the small bowel, in particular, because the WCE is moved by intestinal peristalsis, and does not move based on its own movement, the movement of the WCE cannot be controlled from the external. Therefore, a large number of images are captured in a single examination so as not to miss anything. Furthermore, the number of images captured in a single examination is extremely large because the time for which the WCE moves in the small bowel is about eight hours. For example, because the WCE wirelessly transmits approximately 60,000 images per person, endoscopy specialists check the images by fast-forwarding, and a WCE image analysis with such a number of images requires an intense attention and concentration for a time period of 30 to 120 minutes on the average.

Diagnosing based on such endoscopic images not only requires training of endoscopy specialists and an enormous amount of time for checking the stored images, but also is subjective and the possibility of various false positive and false negative determinations is unavoidable. Furthermore, fatigue of the endoscopy specialists may result in a deterioration in the accuracy of the diagnoses made by the endoscopy specialists. An enormous amount of burden on-site and a deterioration in the accuracy may lead to a restriction imposed on the number of medical examinees, and may result in a lack of sufficient medical services provided based on demands.

In order to reduce the burden and to improve the deterioration in accuracy of endoscopy, there is a high expectation in the use of artificial intelligence (AI). There is an expectation that, if recent AI with an image recognition capability higher than that of humans can be used in assisting endoscopy specialists, it will improve the accuracy and the speed of the secondary interpretations. Recently, AI using deep learning has been attracting attention in various medical fields, and it has been reported that the AI can screen medical images, in replacement of the specialists, not only in the fields such as radiation oncology, skin cancer classifications, diabetic retinopathy (see Non Patent Literatures 1 to 3), and the field of gastroenterological endoscopy, particularly in colonoscopy (see Non Patent Literatures 4 to 6), but also in various medical fields. Furthermore, there are some Patent Literatures in which various types of AI are used in making medical image diagnoses (see Patent Literatures 3 and 4). However, not enough verification has been done on whether the AI's capability of making endoscopic image diagnoses can satisfy an accuracy (correctness) and a performance (speed) requirements usable in the actual medical practice. For this reason, diagnoses based on the endoscopic images with the use of AI have yet to be put into practice.

Deep learning enables a neural network with a plurality of layers stacked to learn high-order features of input data. Deep learning also enables a neural network to update internal parameters that are used in calculating a representation at each layer from the representation at the previous layer, using a back-propagation algorithm, by instructing how the apparatus should make changes.

In establishing associations between medical images, deep learning can train a neural network using medical images accumulated in the past, and has a possibility of being a strong machine-learning technology that allows the clinical features of a patient to be acquired directly from the medical images. A neural network is a mathematical model representing features of a neural circuit of a brain with computational simulations, and the algorithm supporting deep learning takes an approach using a neural network. A convolutional neural network (CNN) is developed by Szegedy, et al., and is a network architecture that is most widely used for a purpose of deep learning of images.

In gastrointestinal endoscopy, a big challenge in making determinations using endoscopic images is how the efficiency can be improved while maintaining a high accuracy. In order to apply AI to such image analyses in this field, improvements in the AI technology have been a big issue. The inventors of the present invention have built a CNN capable of classifying images of esophagus, stomach, and duodenum based on their anatomical sites, and also capable of detecting a stomach cancer in the endoscopic image (see Non Patent Literatures 7 and 8).

Furthermore, the inventors of the present invention have recently reported how a CNN plays a role in making diagnoses of *H. pylori* gastritis based on endoscopic images, indicating that the capability of the CNN came to compare to that of highly experienced endoscopy specialists, and the time required for making diagnoses was reduced significantly (see Non Patent Literature 9). However, because this CNN uses a training/verification data set excluding the cases after the *H. pylori* eradication and including only the cases of *H. pylori* positives and negatives, there is a problem in that it takes time and efforts to build a training/verification data set with the cases after the *H. pylori* eradication excluded, and another problem in that it is impossible to evaluate whether the CNN can correctly identify not only the cases of *H. pylori* positives and negatives, but also the cases after the *H. pylori* eradication.

Furthermore, when CS is to be carried out, practitioners usually examine the rectum, the colon, and a part of the terminal ileum, because clinical characteristics of a disease differ depending on the anatomical sites of the colon and the rectum. For example, according to some recent researches, it has been pointed out that, with regard to colorectal cancers, there are some differences between the right colon and the left colon in epidemiology, prognosis, and a clinical result of chemotherapy. In the same manner, to treat ulcerative colitis, the anatomical site of the large bowel is important. The reason for that is that the applicability of oral drugs and suppositories for ulcerative colitis is also based on the position where the colitis is located. Therefore, in CS examinations, it is clinically meaningful to correctly identify the anatomical sites of colorectal diseases.

CS is generally used in screening for cases of fecal occult blood positives or abdominal symptoms. However, sufficient special training is required for the practitioner to be able to handle a colonoscopy as he/she wishes, to recognize abnormal sites, and to make diagnoses of diseases correctly. One of the reasons why it takes such a long time to acquire the skill is in difficulty in making anatomical recognition in the endoscopy. Due to the anatomical differences between the sites of the colon, and similarity between various parts of the colon, and due to the anatomical differences and similarity between sites of the colons among individuals, not only the beginners of the CS but also the CS specialists cannot recognize the exact position of the tip of the endoscopic scope.

Therefore, in order for a practitioner to perform the CS and to detect abnormality, it is necessary to correctly recognize the anatomical parts of the colon via a CS image. According to some recent evidence, in order to acquire a sufficient skill, at least 200 cases of experiences of completing the entire CS tests are required. In fact, in Japan, certification of endoscopy technique is granted only after endoscope training of 5 years or longer.

Furthermore, the most common symptoms discovered by a WCE in the small bowel is a mucoclasis such as erosion or ulcer. Because erosion and ulcer are mainly caused by a nonsteroidal anti-inflammatory drug (NSAID), and sometimes caused by Crohn's disease or a malignant tumor in the small bowel, an early diagnosis and an early treatment are mandatory. According to various previous reports, because a part of the small bowel where the mucous membrane is destroyed by erosion or ulcer exhibits not much color difference with respect to the normal mucous membrane around such a part, the performance of automatic detection of such parts with the use of software has been lower than that of detections of vasodilatation (see Non Patent Literature 10). Furthermore, no research has been carried out on diagnosing various diseases in the small bowel by applying a CNN to the WCE images of the small bowel.

A superficial esophageal squamous cell carcinoma (hereinafter, sometimes referred to as an SCC) that is defined as a mucosal or submucosal cancer accounts for 38% of all esophageal cancers diagnosed in Japan. For the superficial esophageal SCC, it is possible to apply either esophagectomy or endoscopic resection (ER), but these approaches are very different from each other, from the viewpoint of invasiveness. In the selection of an appropriate treatment, the most important factor is an invasion depth (infiltration depth) of cancer, considering the risk of metastasis or the possibility of healing from the ER.

An endoscopic diagnosis of the invasion depth of a cancer requires sufficient expertise in evaluating various endoscopic opinions, such as the postoperative course, the protrusion, and the hardness of the esophageal cancer, and changes in the microvessels. In a diagnose of the invasion depth of a superficial esophageal SCC, non-magnification endoscopy (non-ME), magnification endoscopy (ME), and endoscopic ultrasound (EUS) are currently used. Diagnoses using non-ME are subjective, and are based on the protrusion, the depression, and the hardness of a cancer, which can be affected by variability among the observers. ME enables a clear observation of microvessel structures that are closely associated with the invasion depth of an esophageal cancer.

Diagnoses using the EUS and the ME are more objective than those with the non-ME, but are more complex, and more affected by the expertise of the physicians. Therefore, reported exact accuracies in the invasion depth of cancers in relation to the EUS and the ME are conflicting and not satisfiable. Therefore, there has been a demand for an innovative approach for facilitating more objective diagnoses of the invasion depths of esophageal cancers.

In addition, there have been some reports that an increased number of superficial non-ampullary duodenal epithelial tumors (SNADETs) are detected due to the recent use of esophagogastroduodenoscopy which covers a wider area in the examinations. Because SNADETs are usually flat and exhibit extremely little changes on the surface, SNADETs are often missed out during the examination. This fact is supported by high variability in the reported detected SNADET ratios which range from 0.1% to 3%. Therefore, there is a demand for a detection method that is effective also in detecting SNADETs using the esophagogastroduodenoscopy.

The present invention is made in consideration of the challenges in the conventional technologies described above. In other words, a first object of the present invention is to provide a diagnostic assistance method, a diagnostic assistance system, a diagnostic assistance program, and a computer-readable recording medium storing therein the diagnostic assistance program for a disease based on an endoscopic image of a digestive organ, being capable of correctly identifying, for example, not only the cases of *H. pylori* positives and negatives but also cases after *H. pylori* eradication, using an endoscopic image of the digestive organ with use of a CNN.

A second object of the present invention is to provide a diagnostic assistance method, a diagnostic assistance system, a diagnostic assistance program, and a computer-readable recording medium storing therein the diagnostic assistance program for a disease based on an endoscopic image of a digestive organ, being capable of identifying, for example, the anatomical site of a colorectal disease, using an endoscopic image of a digestive organ with use of a CNN.

A third object of the present invention is to provide a diagnostic assistance method, a diagnostic assistance system, a diagnostic assistance program, and a computer-readable recording medium storing therein the diagnostic assistance program for a disease in the small bowel based on an endoscopic image of the small bowel with a WCE, being capable of correctly identifying erosion/ulcer in the small bowel with use of a CNN.

A fourth object of the present invention is to provide a diagnostic assistance method, a diagnostic assistance system, a diagnostic assistance program, and a computer-readable recording medium storing therein the diagnostic assistance program for a superficial esophageal SCC based on an endoscopic image of the esophagus, using non-ME and ME, being capable of detecting the invasion depth of and classifying the superficial esophageal SCC.

Furthermore, a fifth object of the present invention is to provide a diagnostic assistance method, a diagnostic assistance system, a diagnostic assistance program, and a computer-readable recording medium storing therein the diagnostic assistance program for SNADET, based on an endoscopic image of duodenum, with use of esophagogastroduodenoscopy.

A diagnostic assistance method for a disease based on an endoscopic image of a digestive organ with use of a convolutional neural network (hereinafter, sometimes referred to as a "CNN") according to a first aspect of the present invention is a diagnostic assistance method for a disease based on an endoscopic image of a digestive organ with use of a CNN, the diagnostic assistance method is characterized by including:

training the CNN using
　a first endoscopic image of the digestive organ, and
　at least one final diagnosis result on positivity or negativity to the disease in the digestive organ, a past disease, a severity level, an invasion depth of the disease, and information corresponding to a site where an image is captured, the final diagnosis result being corresponding to the first endoscopic image, in which the trained CNN outputs at least one of a probability of the positivity and/or the negativity to the disease in the digestive organ, a probability of the past disease, the severity level of the disease, the invasion depth of the disease, and a probability corresponding to the site where the image is captured, based on a second endoscopic image of the digestive organ.

With the diagnostic assistance method for a disease based on an endoscopic image of a digestive organ with use of a CNN according to the present aspect, because the CNN is trained based on the first endoscopic image including a plurality of the endoscopic images of the digestive organ that are acquired for each of a plurality of subjects in advance, and on the at least one final diagnosis result on the positivity or negativity to the disease, the past disease, the severity level, the invasion depth of the disease, and the information corresponding to the site where the image is captured, the final diagnosis result having been acquired in advance for each of the subjects, it is possible to acquire one or more of the probability of the positivity and/or the negativity to the disease in the digestive organ, the probability of the past disease, the severity level of the disease, the invasion depth of the disease, and the probability corresponding to the site where the image is captured, of the subject, at an accuracy substantially comparable to that of an endoscopy specialist within a short time period. Therefore, a subject requiring a separate confirmation diagnosis can be selected. Moreover, because it becomes possible to achieve an automatic diagnosis of at least one of the probability of the positivity and/or the negativity to the disease, the probability of the past disease, the severity level of the disease, the invasion depth of the disease, and the probability corresponding to the site where the image is captured, for test data including the endoscopic images of the digestive organ of a large number of subjects, not only an endoscopy specialist is enabled to perform check and make corrections easily, but also it becomes possible to simplify the tasks of creating a collection of images that are associated with a disease.

Furthermore, a diagnostic assistance method for a disease based on an endoscopic image of a digestive organ with use of a CNN according to a second aspect of the present invention is, in the diagnostic assistance method for a disease based on an endoscopic image of a digestive organ with use of a CNN according to the first aspect, characterized in that the first endoscopic image is associated with a site of a digestive organ where the image is captured.

An untrained CNN sometimes has difficulty in identifying the site where an endoscopic image of a specific digestive organ is captured. With the diagnostic assistance method for a disease in a digestive organ with use of a CNN according to the second aspect, because the neural network is trained with the endoscopic images classified into the respective sites, it becomes possible to train the CNN finely correspondingly to the sites, so that it becomes possible to improve the detection accuracy of the probability of the negativity or the positivity to the disease, the probability of the past disease, the severity level of the disease, the probability corresponding to the site where the image is captured, for the second endoscopic image.

Furthermore, a diagnostic assistance method for a disease based on an endoscopic image of a digestive organ with use of a CNN according to a third aspect of the present invention is, in the diagnostic assistance method for a disease based on an endoscopic image a digestive organ with use of a CNN according to the second aspect, characterized in that the site of the digestive organ includes at least one of the pharynx, the esophagus, the stomach, the duodenum, the small bowel, and the large bowel.

With the diagnostic assistance method for a disease based on an endoscopic image of a digestive organ with use of a CNN according to the third aspect, because the sites can be correctly classified into the pharynx, the esophagus, the stomach, the duodenum, and the large bowel, it is possible to improve the detection accuracy of the probability of the positivity and the negativity to the disease, the probability of the past disease, the severity level of the disease, the probability corresponding to the site where the image is captured, for each of the sites.

Furthermore, a diagnostic assistance method for a disease based on an endoscopic image of a digestive organ with use of a CNN according to a fourth aspect of the present invention is, in the diagnostic assistance method for a disease based on an endoscopic image of a digestive organ with use of a CNN according to the third aspect, characterized in that the site of the digestive organ is sectioned into a plurality of sections in at least one of the pharynx, the esophagus, the stomach, the duodenum, the small bowel, and the large bowel.

Because every digestive organ has a complex shape, if only a small number of sites to be classified are available, it is sometimes difficult to recognize to which site of the digestive organ a specific endoscopic image corresponds. In the diagnostic assistance method for a disease based on an endoscopic image of a digestive organ with use of a CNN according to the fourth aspect, because each of digestive organs is sectioned into the sections, it becomes possible to achieve a highly accurate diagnosis result within a short time period.

Furthermore, a diagnostic assistance method for a disease based on an endoscopic image of a digestive organ with use of a CNN according to a fifth aspect of the present invention is, in the diagnostic assistance method for a disease based on an endoscopic image of a digestive organ with use of a CNN according to the third or the fourth aspect, characterized in that the site of the digestive organ is stomach, the at least one final diagnosis result includes at least one of positive *H. pylori* infection, negative *H. pylori* infection, and *H. pylori* eradicated, and the CNN outputs at least one of a probability of the positive *H. pylori* infection, a probability of the negative *H. pylori* infection, and a probability of the *H. pylori* eradicated.

With the diagnostic assistance method for a disease based on an endoscopic image of a digestive organ with use of a CNN according to the fifth aspect of the present invention, it is possible to output not only the probabilities of the positive *H. pylori* infection or negative *H. pylori* infection of the subject, but also a probability of the subject having gone through the *H. pylori* eradication, within an extremely short time period, at the accuracy equivalent to that of a specialist in the Japan Gastroenterological Endoscopy Society. Therefore, a subject requiring a separate confirmation diagnosis can be selected correctly within a short time period. It is possible to make the confirmation diagnosis by subjecting the selected subject to a measurement of an anti-*H. pylori* IgG level in the blood or urine, coproantibody test, or a urea breath test.

Furthermore, a diagnostic assistance method for a disease based on an endoscopic image a digestive organ with use of a CNN according to a sixth aspect of the present invention is, in the diagnostic assistance method for a disease based on an endoscopic image of a digestive organ with use of a CNN according to the fourth aspect, characterized in that the site of the digestive organ is the large bowel; the section is at least one of the terminal ileum, the cecum, the ascending colon, the transverse colon, the descending colon, the sigmoid colon, rectum, and the anus; and the CNN outputs a probability corresponding to at least one of the terminal ileum, the cecum, the ascending colon, the transverse colon, the descending colon, the sigmoid colon, the rectum, and the anus, as the section where the second endoscopic image is captured.

Furthermore, a diagnostic assistance method for a disease based on an endoscopic image of a digestive organ with use of a CNN according to a seventh aspect of the present invention is, in the diagnostic assistance method for a disease based on an endoscopic image of a digestive organ with use of a CNN according to the fourth aspect, characterized in that the site of the digestive organ is the large bowel; and the sections are the terminal ileum, the cecum, the ascending colon and transverse colon, the descending colon and sigmoid colon, and the rectum, and the anus; and the CNN outputs a probability corresponding to at least one of the terminal ileum, the cecum, the ascending colon and transverse colon, the descending colon and sigmoid colon, and the rectum, and the anus, as the section where the second endoscopic image is captured.

Furthermore, a diagnostic assistance method for a disease based on an endoscopic image of a digestive organ with use of a CNN according to an eighth aspect of the present invention is, in the diagnostic assistance method for a disease based on an endoscopic image of a digestive organ with use of a CNN according to the fourth aspect, characterized in that the site of the digestive organ is the large bowel; the sections are the terminal ileum, the right colon including the cecum-ascending colon-transverse colon, and the left colon including the descending colon-sigmoid colon-rectum, and the anus; and the CNN outputs a probability corresponding to at least one of the terminal ileum, the right colon including the cecum-ascending colon-transverse colon, and the left colon including the descending colon-sigmoid colon-rectum, and the anus, as the section where the second endoscopic image is captured.

With the diagnostic assistance method for a disease based on an endoscopic image of a digestive organ with use of a CNN according to any one of the sixth to the eighth aspects of the present invention, because the sections of the large bowel can be classified correctly, it becomes possible to understand the section requiring a detailed examination. The sections of the large bowel may be selected considering the appearance tendency, appearance frequency, and the like of large bowel diseases, and considering sensitivities of the CNN and degrees of specificity corresponding to the respective sections.

Furthermore, a diagnostic assistance method for a disease based on an endoscopic image of a digestive organ with use of a CNN according to a ninth aspect of the present invention is, in the diagnostic assistance method for a disease based on an endoscopic image of a digestive organ with use of a CNN according to the third aspect, characterized in that the site of the digestive organ is the small bowel; the endoscopic image is a wireless-capsule endoscopic image; and the disease is at least one of erosion and ulcer.

With the diagnostic assistance method for a disease based on an endoscopic image of a digestive organ with use of a CNN according to the ninth aspect of the present invention, for WCE endoscopic images of the small bowel acquired from a large number of subjects, it becomes possible to acquire a region and probability of the positivity and/or negativity to a disease in the small bowel of the subjects, at an accuracy substantially comparable to that of an endoscopy specialist, within a short time period. Therefore, a subject requiring a separate confirmation diagnosis can be selected within a short time period, and an endoscopy specialist is enabled to perform check and make corrections easily. With the diagnostic assistance method for a disease based on an endoscopic image of a digestive organ with use of a CNN according to the present aspect, although the erosion and the ulcer are not clearly distinguishable in a WCE endoscopic image of the small bowel, at least one of the erosion and the ulcer can be selected automatically and correctly.

Furthermore, a diagnostic assistance method for a disease based on an endoscopic image of a digestive organ with use of a CNN according to a tenth aspect of the present invention is, in the diagnostic assistance method for a disease based on an endoscopic image of a digestive organ with use of a CNN according to the third aspect, characterized in that the site of the digestive organ is duodenum; the endoscopic image is an esophagogastroduodenoscopic image; and the disease is a superficial non-ampullary duodenal epithelial tumor.

With the diagnostic assistance method for a disease based on an endoscopic image of a digestive organ with use of a CNN according to the tenth aspect of the present invention, a region and a probability of the superficial non-ampullary duodenal epithelial tumor can be acquired within a short time period, for an endoscopic image achieved by esophagogastroduodenoscopy.

A diagnostic assistance method for a disease based on an endoscopic image of a digestive organ with use of a CNN according to an eleventh aspect of the present invention is, in the diagnostic assistance method for a disease based on an endoscopic image of a digestive organ with use of a CNN according to the ninth or the tenth aspect, characterized in that the final diagnosis result on the positivity or the negativity to the disease is displayed as a disease-positive region in the second endoscopic image; the trained convolutional neural network displays the disease-positive region thus detected in the second endoscopic image, and also displays a probability score in the second image.

With the diagnostic assistance method for a disease based on an endoscopic image of a digestive organ with use of a CNN according to the eleventh aspect of the present invention, because the region from which an endoscopy specialist has acquired the final diagnosis result can be compared correctly with the disease-positive region detected by the trained CNN in the second endoscopic image, better CNN sensitivity and the degree of specificity can be achieved.

Furthermore, a diagnostic assistance method for a disease based on an endoscopic image of a digestive organ with use of a CNN according to a twelfth aspect of the present invention is, in the diagnostic assistance method for a disease based on an endoscopic image of a digestive organ with use of a CNN according to the eleventh aspect, characterized in that a determination as to whether a result diagnosed by the trained convolutional neural network is correct, based on an overlap between the disease-positive region displayed in the second endoscopic image, being displayed as the final diagnosis result on the positivity or the negativity to the disease, and the disease-positive region displayed by the trained convolutional neural network in the second endoscopic image.

With the diagnostic assistance method for a disease based on an endoscopic image of a digestive organ with use of a CNN according to the twelfth aspect of the present invention, because the region from which an endoscopy specialist has acquired the final diagnosis result and the disease-positive region detected by the trained CNN are both displayed in the second endoscopic image, comparisons with the diagnosis result of the trained CNN can be performed immediately, based on the overlap of such regions.

Furthermore, a diagnostic assistance method for a disease based on an endoscopic image of a digestive organ with use of a CNN according to a thirteenth aspect of the present invention is, in the diagnostic assistance method for a disease based on an endoscopic image of a digestive organ with use of a CNN according to twelfth aspect, characterized in that, (1) when the overlap occupies 80% or more of the disease-positive region displayed in the second endoscopic image, as the final diagnosis result on the positivity or the negativity to the disease in the small bowel, or (2) when a plurality of the disease-positive regions are displayed by the trained convolutional neural network in the second endoscopic image, and one of the regions overlaps with the disease-positive region displayed in the first endoscopic image, as the final diagnosis result on the positivity or the negativity to the disease, the diagnosis made by the trained convolutional neural network is determined to be correct.

With the diagnostic assistance method for a disease based on an endoscopic image of a digestive organ with use of a CNN according to the thirteenth aspect of the present invention, the correctness of the diagnosis made by the CNN can be determined easily, so that the accuracy of the diagnosis made by the trained CNN is improved.

Furthermore, a diagnostic assistance method for a disease based on an endoscopic image of a digestive organ with use of a CNN according to a fourteenth aspect of the present invention is, in the diagnostic assistance method for a disease based on an endoscopic image of a digestive organ with use of a CNN according to any one of the ninth to the thirteenth aspects, characterized in that the trained convolutional neural network displays a probability score as well as the detected disease-positive region in the second image.

With the diagnostic assistance method for a disease based on an endoscopic image of a digestive organ with use of a CNN according to the fourteenth aspect of the present invention, an endoscopy specialist is enabled to, for a large number of subjects, get grasp of the region of the positivity and/or the negativity to the disease in the small bowel or the duodenum, and the probability score correctly, within a short time period, so that an endoscopy specialist is enabled to perform check and make a correction easily.

Furthermore, a diagnostic assistance method for a disease based on an endoscopic image of a digestive organ with use of a CNN according to a fifteenth aspect of the present invention is, in the diagnostic assistance method for a disease based on an endoscopic image of a digestive organ with use of a CNN according to the third aspect, characterized in that the site of the digestive organ is esophagus; the endoscopic image is a non-magnification endoscopic image or a magnification endoscopic image; and the disease is an invasion depth of a superficial esophageal squamous cell carcinoma (SCC). Furthermore, a diagnostic assistance method for a disease based on an endoscopic image of a digestive organ with use of a CNN according to a sixteenth aspect of the present invention is, in the diagnostic assistance method for a disease based on an endoscopic image of a digestive organ with use of a CNN according to the fifteenth aspect, characterized in that the final diagnosis result on the positivity or the negativity to the disease is used to determine that the invasion depth of the squamous cell carcinoma is one of a mucosal epithelium-lamina propria mucosa (EP-LPM), a muscularis mucosa (MM), a section near a surface of a submucosal layer (SM1), and a level deeper than an intermediary portion of the submucosal layer (SM2-).

With the diagnostic assistance method for a disease based on an endoscopic image of a digestive organ with use of a CNN according to the fifteenth or the sixteenth aspect of the present invention, because it is possible to get grasp of the invasion depth of the superficial esophageal SCC correctly within a short time period, the determination of the applicability of endoscopic resection (ER) to the superficial esophageal SCC can be made correctly.

Furthermore, a diagnostic assistance method for a disease based on an endoscopic image of a digestive organ with use of a CNN according to a seventeenth aspect of the present invention is, in the diagnostic assistance method for a disease based on an endoscopic image of a digestive organ with use of a CNN according to any one of the first to the sixteenth aspects, characterized in that the CNN is also combined with three dimensional information from an X-ray computer tomographic imaging apparatus, an ultrasound computer tomographic imaging apparatus, or a magnetic resonance imaging diagnosis apparatus.

Because an X-ray computer tomographic imaging apparatus, an ultrasound computer tomographic imaging apparatus, and a magnetic resonance imaging diagnosis apparatus are capable of representing the structures of the digestive organs three dimensionally, it becomes possible to get grasp of the site where the endoscopic image is captured, more correctly, by combining the three dimensional information with the output of the CNN according to any one of the first to the sixteenth aspects.

Furthermore, a diagnostic assistance method for a disease based on an endoscopic image of a digestive organ with use of a CNN according to an eighteenth aspect of the present invention is, in the diagnostic assistance method for a disease based on an endoscopic image of a digestive organ with use of a CNN according to any one of the first to the seventeenth aspects, characterized in that the second endoscopic image is at least one of an image captured by an endoscope, an image transmitted over a communication network, an image provided by a remote control system or a cloud system, an image recorded in a computer-readable recording medium, and a video.

With the diagnostic assistance method for a disease based on an endoscopic image of a digestive organ with use of a CNN according to the eighteenth aspect, because it is possible to output the probability of the positivity and the negativity to the disease in the digestive organ, or the severity of the a disease within a short time period, for the input second endoscopic image, regardless of the way in which the second endoscopic image is input, e.g., even when the image is transmitted from a remote location, or even when the image is a video. As the communication network, the Internet, an intranet, an extranet, a local area network (LAN), an integrated services digital network (ISDN), a value-added network (VAN), a cable television (CATV) communication network, a virtual private network, a telephone network, a mobile communication network, a satellite communication network, and the like, which are known, may also be used. Furthermore, as the transmission medium of the communication network, a known wired transmission such as via an IEEE1394 serial bus, an USB, a powerline transmission, a cable TV circuit, a telephone network, and an ADSL line, wireless transmission such as via infrared, Bluetooth (registered trademark), and IEEE802.11, or a wireless transmission such as a mobile telephone network, a satellite circuit, and a terrestrial digital network may also be used. In this manner, this method may be used in a configuration as what is called a cloud service or remote assistance service.

Furthermore, it is also possible to use known tapes such as a magnetic tape or a cassette tape, disks including magnetic disks such as a floppy (registered trademark) disk or a hard disk, discs including optical discs such as a compact disc read-only memory (CD-ROM)/a magneto-optical (MO) disc/a MiniDisc (MD: registered trademark)/a digital video disc/a compact disc recordable (CD-R), cards such as an integrated circuit (IC) card, a memory card, and an optical card, or semiconductor memories such as a mask ROM/an erasable programmable read-only memory (EPROM)/an electrically erasable programmable read-only memory (EEPROM)/a flash ROM. With them, it is possible to provide a configuration for enabling the system to be transferred or installed in what is called a medical care organization or a health check organization.

A diagnostic assistance system for a disease based on an endoscopic image of a digestive organ according to a nineteenth aspect of the present invention is a diagnostic assistance system for a disease based on an endoscopic image of an endoscopic image, the diagnostic assistance system including an endoscopic image input unit, an output unit, and a computer incorporated with a CNN, characterized in that the computer includes:
  a first storage area that stores therein first endoscopic images of a digestive organ;
  a second storage area that stores therein at least one of at least one final diagnosis result on positivity or negativity to the disease in the digestive organ, a past disease, a severity level, an invasion depth of the disease, and information corresponding to a site where an image is captured, the final diagnosis result being corresponding to the first endoscopic image; and a third storage area that stores therein a program of the CNN, and the CNN is trained based on the first endoscopic image stored in the first storage unit, and the final diagnosis result stored in the second storage area, and outputs at least one of a probability of the positivity and/or the negativity to the disease in the digestive organ, a probability of the past disease, a severity level of the disease, an invasion depth of the disease, and a probability corresponding to the site where the image is captured, for the second endoscopic image, to the output unit, based on a second endoscopic image of the digestive organ, the second endoscopic image being input from the endoscopic image input unit.

Furthermore, a diagnostic assistance system for a disease based on an endoscopic image of a digestive organ according to a twentieth aspect of the present invention is, in the diagnostic assistance system for a disease based on an endoscopic image of a digestive organ according to the eighteenth aspect of the present invention, characterized in that the first endoscopic images are associated with respective sites where the images are captured.

Furthermore, a diagnostic assistance system for a disease based on an endoscopic image of a digestive organ according to a twenty first aspect of the present invention is, in the diagnostic assistance system for a disease based on an endoscopic image of a digestive organ according to the twentieth aspect of the present invention, characterized in that the site of the digestive organ includes at least one of the pharynx, the esophagus, the stomach, the duodenum, the small bowel, and the large bowel.

Furthermore, a diagnostic assistance system for a diagnosis based on an endoscopic image of a digestive organ according to a twenty second aspect of the present invention is, in the diagnostic assistance system for a diagnosis based on an endoscopic image of a disease in a digestive organ according to the twenty first aspect of the present invention, characterized in that the site of the digestive organ is sectioned into a plurality of sections in at least one of the pharynx, the esophagus, the stomach, the duodenum, the small bowel, and the large bowel.

Furthermore, a diagnostic assistance system for a disease based on an endoscopic image of a digestive organ according to a twenty third aspect of the present invention is, in the diagnostic assistance system for a disease based on an endoscopic image of a digestive organ according to the twenty first or the twenty second aspect of the present invention, characterized in that the site of the digestive organ is the stomach; and the CNN outputs at least one of a probability of positive *H. pylori* infection, a probability of negative *H. pylori* infection, and a probability of *H. pylori* eradicated, based on the second endoscopic image.

Furthermore, a diagnostic assistance system for a disease based on an endoscopic image of a digestive organ according to a twenty fourth aspect of the present invention is, in the diagnostic assistance system for a disease based on an endoscopic image of a digestive organ according to the twenty second aspect of the present invention, characterized in that the site of the digestive organ is the large bowel; the section is at least one of the terminal ileum, the cecum, the ascending colon, the transverse colon, the descending colon, the sigmoid colon, the rectum, and the anus; the CNN outputs a probability corresponding to at least one of the terminal ileum, the cecum, the ascending colon, the transverse colon, the descending colon, the sigmoid colon, the rectum, and the anus, as the section where the second endoscopic image is captured.

Furthermore, a diagnostic assistance system for a disease based on an endoscopic image of a digestive organ according to a twenty fifth aspect of the present invention is, in the diagnostic assistance system for a disease based on an endoscopic image of a digestive organ according to the twenty second aspect of the present invention, characterized in that the site of the digestive organ is the large bowel; the section is at least one of the terminal ileum, the cecum, the ascending colon, the transverse colon, the descending colon, the sigmoid colon, the rectum, and the anus; and the CNN outputs a probability corresponding to at least one of the terminal ileum, the cecum, the ascending colon and transverse colon, the descending colon and sigmoid colon, and the rectum, and the anus, as the site where the second endoscopic image is captured.

Furthermore, a diagnostic assistance system for a disease based on an endoscopic image of a digestive organ according to a twenty sixth aspect of the present invention is, in the diagnostic assistance system for a disease based on an endoscopic image of a digestive organ according to the twenty second aspect of the present invention, characterized in that the site of the digestive organ is the large bowel; and the trained CNN outputs a probability corresponding to at least one of the sections of the terminal ileum, the right colon including the cecum-ascending colon-transverse colon, and the left colon including the descending colon-sigmoid colon-rectum, and the anus, as the site where the second endoscopic image is captured.

Furthermore, a diagnostic assistance system for a disease based on an endoscopic image of a digestive organ according to a twenty seventh aspect of the present invention is, in the diagnostic assistance system for a disease based on an endoscopic image of a digestive organ according to the twenty first aspect of the present invention, characterized in that the site of the digestive organ is the small bowel; and the trained convolutional neural network outputs a probability corresponding to at least one of erosion and ulcer as the disease, based on the second endoscopic image.

Furthermore, a diagnostic assistance system for a disease based on an endoscopic image of a digestive organ according to a twenty eighth aspect of the present invention is, in the diagnostic assistance system for a disease based on an endoscopic image of a digestive organ according to the twenty first aspect of the present invention, characterized in that the site of the digestive organ is the duodenum, the trained convolutional neural network outputs a probability corresponding to a superficial non-ampullary duodenal epithelial tumor as the disease, based on the second endoscopic image.

Furthermore, a diagnostic assistance system for a disease based on an endoscopic image of a digestive organ according to a twenty ninth aspect of the present invention is, in the diagnostic assistance system for a disease based on an endoscopic image of a digestive organ according to any one of the nineteenth to the twenty eighth aspect of the present invention, characterized in that the CNN is combined with three dimensional information from an X-ray computer tomographic imaging apparatus, an ultrasound computer tomographic imaging apparatus, or a magnetic resonance imaging diagnosis apparatus.

Furthermore, a diagnostic assistance system for a disease based on an endoscopic image of a digestive organ according to a thirtieth aspect of the present invention is, in the diagnostic assistance system for a disease based on an endoscopic image of a digestive organ according to any one of the nineteenth to the twenty eighth aspects of the present invention, characterized in that the second endoscopic image is at least one of an image captured by an endoscope, an image transmitted over a communication network, an image provided by a remote control system or a cloud system, an image recorded in a computer-readable recording medium, and a video.

With the diagnostic assistance system for a disease based on an endoscopic image of a digestive organ according to any one of the nineteenth to the thirtieth aspect of the present invention, it is possible to achieve the same effects as those achieved by the diagnostic assistance method for a disease based on an endoscopic image of a digestive organ with use of a CNN according to any one of the first to the eighteenth aspects.

Furthermore, a diagnostic assistance program based on an endoscopic image of a digestive organ according to a thirty first aspect of the present invention is characterized by being intended to cause a computer to operate as units included in the diagnostic assistance system for a disease based on an endoscopic image of a digestive organ according to any one of the nineteenth to the twenty eighth aspects.

With the diagnostic assistance program based on an endoscopic image of a digestive organ according to the thirty first aspect of the present invention, it is possible to provide a diagnostic assistance program based on an endoscopic image, the diagnostic assistance program intended to cause a computer to operate as the units included in the diagnostic assistance system based on an endoscopic image of a digestive organ according to any one of the nineteenth to the twenty eighth aspects.

Furthermore, a computer-readable recording medium according to a thirty second aspect of the present invention stores therein the diagnostic assistance program based on an endoscopic image of a digestive organ according to the thirty first aspect.

With the computer-readable recording medium according to the thirty second aspect of the present invention, it is possible to provide a computer-readable recording medium storing therein the diagnostic assistance program based on an endoscopic image of a digestive organ according to the thirty first aspect.

Advantageous Effects of Invention

As described above, according to the present invention, because a computer program incorporated with a CNN is trained based on a plurality of endoscopic images of a digestive organ, acquired for each of a plurality of subjects in advance, and a final diagnosis result on positivity or negativity to the disease, acquired for each of the subjects in advance, it is possible to acquire the probability of the positivity and/or the negativity to the disease in the digestive organ of the subject, the probability of the past disease, the severity level of the disease, the invasion depth of the disease, the information corresponding to a site where an image is captured, and the like, within a short time period, at an accuracy substantially comparable to that of an endoscopy specialist. Therefore, a subject requiring a separate confirmation diagnosis can be selected.

BRIEF DESCRIPTION OF DRAWINGS

FIG. 7 is a view illustrating a typical colonoscopic image, and probability scores of respective sites recognized by the CNN according to the second embodiment.

FIG. 8A is a view illustrating receiver operating characteristic (ROC) curves of the terminal ileum, the cecum, the ascending colon, the descending colon, the sigmoid colon, and the rectum, and the anus, respectively.

FIG. 8B is a view illustrating receiver operating characteristic (ROC) curves of the terminal ileum, the cecum, the ascending colon, the descending colon, the sigmoid colon, and the rectum, and the anus, respectively.

FIG. 8C is a view illustrating receiver operating characteristic (ROC) curves of the terminal ileum, the cecum, the ascending colon, the descending colon, the sigmoid colon, and the rectum, and the anus, respectively.

FIG. 8D is a view illustrating receiver operating characteristic (ROC) curves of the terminal ileum, the cecum, the ascending colon, the descending colon, the sigmoid colon, and the rectum, and the anus, respectively.

FIG. 8E is a view illustrating receiver operating characteristic (ROC) curves of the terminal ileum, the cecum, the ascending colon, the descending colon, the sigmoid colon, and the rectum, and the anus, respectively.

FIG. 8F is a view illustrating receiver operating characteristic (ROC) curves of the terminal ileum, the cecum, the ascending colon, the descending colon, the sigmoid colon, and the rectum, and the anus, respectively.

FIG. 12 is a view illustrating one example of a ROC curve achieved by the CNN according to the third embodiment.

FIG. 13A is a views illustrating typical enteroscopic images, diagnosed correctly by the CNN according to the third embodiment, and probability scores of specific sites recognized by the CNN.

FIG. 13B is a view illustrating typical enteroscopic images, diagnosed correctly by the CNN according to the third embodiment, and probability scores of specific sites recognized by the CNN.

FIG. 13C is a view illustrating typical enteroscopic images, diagnosed correctly by the CNN according to the third embodiment, and probability scores of specific sites recognized by the CNN.

FIG. 13D is a view illustrating typical enteroscopic images, diagnosed correctly by the CNN according to the third embodiment, and probability scores of specific sites recognized by the CNN.

FIG. 14A is an examples of images diagnosed as a false positive by the CNN according to the third embodiment, due to darkness, laterality, bubbles, fragments, and vasodilatation, respectively;

FIG. 14B is an example of images diagnosed as a false positive by the CNN according to the third embodiment, due to darkness, laterality, bubbles, fragments, and vasodilatation, respectively;

FIG. 14C is an example of images diagnosed as a false positive by the CNN according to the third embodiment, due to darkness, laterality, bubbles, fragments, and vasodilatation, respectively;

FIG. 14D is an example of images diagnosed as a false positive by the CNN according to the third embodiment, due to darkness, laterality, bubbles, fragments, and vasodilatation, respectively;

FIG. 14E is an example of images diagnosed as a false positive by the CNN according to the third embodiment, due to darkness, laterality, bubbles, fragments, and vasodilatation, respectively FIG. 14F is an examples of images of true erosion but diagnosed as a false positive.

FIG. 14G is an example of images of true erosion but diagnosed as a false positive.

FIG. 14H is an example of images of true erosion but diagnosed as a false positive.

FIG. 15 is a schematic sectional view for explaining a relation between the invasion depth of superficial squamous cell carcinoma (SCC) of the esophagus, and its classification, to which the CNN according to a fourth embodiment is applied.

FIG. 16 is a view illustrating main anatomical sites of the duodenum.

FIG. 19A is an endoscopic image for which the CNN according to the fifth embodiment failed to recognize any lesion;

FIG. 19B is an endoscopic image for which a negative determination was made due to a low probability score though a lesion was successfully recognized by the CNN.

FIG. 20 is a block diagram of a diagnostic assistance method for a disease based on an endoscopic image of a digestive organ with use of a neural network according to a sixth embodiment.

FIG. 21 is a block diagram related to a diagnostic assistance system for a disease based on an endoscopic image of a digestive organ, a diagnostic assistance program based on an endoscopic image of a digestive organ, and a computer-readable recording medium, according to a seventh embodiment.

DETAILED DESCRIPTION

A diagnostic assistance method, a diagnostic assistance system, a diagnostic assistance program, and a computer-readable recording medium storing therein the diagnostic assistance program for a disease based on an endoscopic image of a digestive organ, according to the present invention will now be explained in detail, using an example of gastritis induced by *H. pylori* infection, and an example of recognizing large bowel sites. The embodiments described below, however, are merely examples for substantiating the technical idea according to the present invention, and the scope of the present invention is not intended to be limited to these examples. In other words, the present invention is also equally applicable to other embodiments that fall within the scope defined in the appended claims. Furthermore, in the present invention, the term "image" includes video as well as still images.

First Embodiment

In a first embodiment, a diagnostic assistance method, a diagnostic assistance system, a diagnostic assistance program, and a computer-readable recording medium storing therein the diagnostic assistance program for a disease based on an endoscopic image of a digestive organ, according to the present invention will be explained, as an example of application to gastritis caused by *H. pylori* infection. In the clinic to which one of the inventors of the present invention belongs, 33 endoscopic doctors in total carried out esophagogastroduodenoscopic examinations (hereinafter, referred to as "EGD") using an endoscope with an ordinary magnification with white light. Indications for the applications of EGD included various symptoms in the upper abdomen, a positive result in barium examinations for stomach diseases, abnormal serum pepsinogen levels, past diseases in the stomach or duodenum, or referrals concerning screening from primary care physicians.

The EGD was carried out by capturing images using a standard EGD endoscope (EVIS GIF-XP290N, GIF-XP260, GIF-XP260NS, GIF-N260; Olympus Medical Systems Corp., Tokyo) with the white light. The acquired images were those captured at an ordinary magnification, and no enlarged image was used.

Figure 1A:
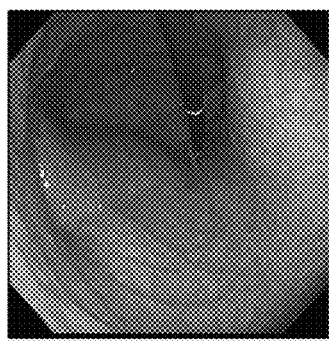
FIG. 1A is an example of a gastroscopic image with positive *H. pylori* infection.
Figure 1B:
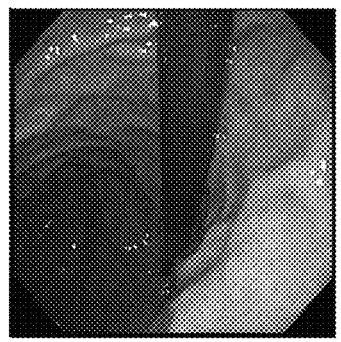
FIG. 1B is an example of a gastroscopic image with negative *H. pylori* infection.
Figure 1C:
FIG. 1C is an example of a gastroscopic image after *H. pylori* eradication.

All of the patients received an examination to find out whether there was an *H. pylori* infection. The examination included at least one of a measurement of the anti-*H. pylori* IgG level in the blood or the urine, coproantibody measurement, and a urea breath test. The patients who exhibited positive reaction in any of these examinations were classified as *H. pylori* positive. The patients who were not diagnosed as *H. pylori* positive and who had no experience of receiving *H. pylori* eradication treatment were classified as *H. pylori* negative. The patients who had received the *H. pylori* eradication treatment in the past and whose *H. pylori* was successfully eradicated were classified as *H. pylori* eradicated. FIG. 1 illustrates acquired endoscopic images representing typical stomach sites. FIG. 1A is an example of an image diagnosed as *H. pylori* positive. FIG. 1B is an example of an image diagnosed as *H. pylori* negative, and FIG. 1C is an example of an image after the *H. pylori* eradication.

[About Data Sets]

By retroactively reviewing images of 5,236 patients who received an EGD during the period between December 2015 and April 2017, data sets to be used for training and verifying an AI-based diagnostic system were prepared (these data sets will be hereinafter referred to as a "training data set" and a "verification data set", and collectively referred to as a "training/verification data set". The training and verification are sometimes collectively referred to as "training/verification"). The data of patients who had stomach cancer, ulcer, or submucosal tumor, and those who had a history of these diseases were excluded from the training/verification data set. The images of the stomach diagnosed with H. pylori positive, H. pylori negative, or H. pylori eradicated were further screened by endoscopy specialists to exclude unclear images due to food residue or bleeding in the stomach, or halation. An endoscopic image data set to be evaluated (hereinafter, referred to as a "test data set") was also prepared. This "training/verification data" corresponds to a "first endoscopic image" according to the present invention, and the "test data" corresponds to a "second endoscopic image" according to the present invention.

Figure 2:
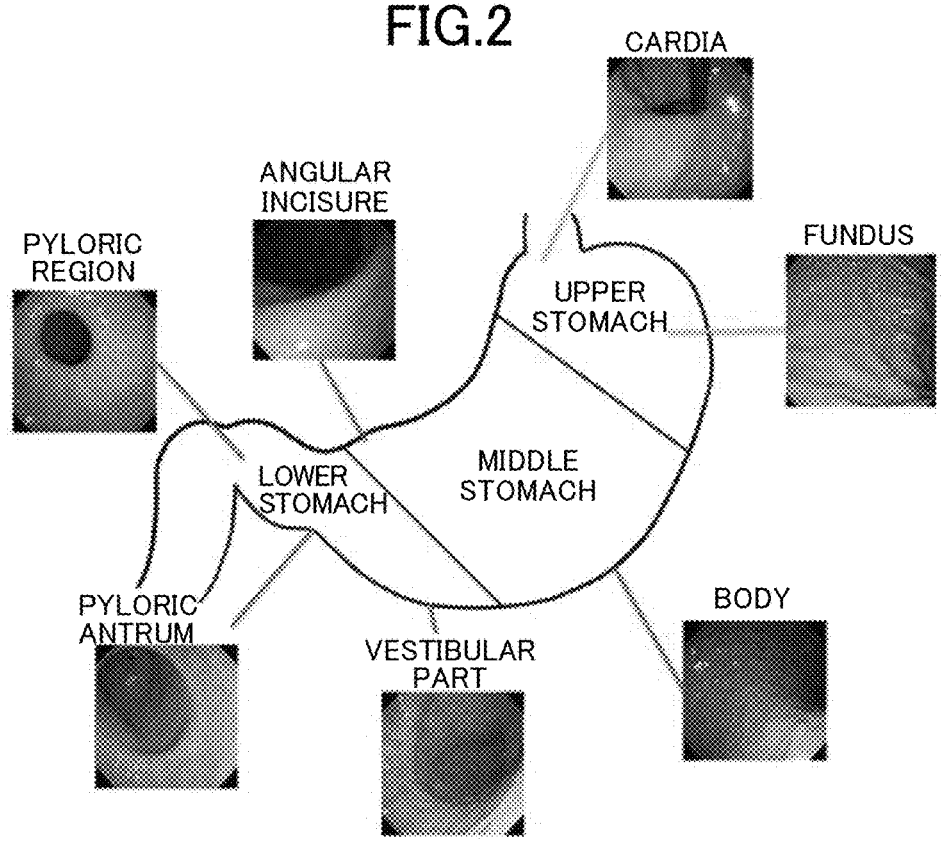
FIG. 2 is a schematic illustrating main anatomical sites of the stomach.

As indicated in Table 1, 98,564 images acquired from 742 patients who were determined as H. pylori positive, 3,469 patients who were determined as H. pylori negative, and 845 patients who were determined as H. pylori eradicated were prepared for the training data set. The number of images was then increased by rotating the 98,564 endoscopic images randomly, at an angle between 0 and 359°, by trimming and deleting the black frame portions around the images, and decreasing or increasing the scale of the resultant images within a range of 0.9 times to 1.1 times, as appropriate. The number of images can be increased by at least one of rotating, increasing or decreasing the scale, changing the number of pixels, extracting bright or dark portions, and extracting the sites with a color tone change, and can be increased automatically using some tool. It is also possible to exclude emphasized images such as narrow-band images, so that the training data set includes only ordinary white light images at an ordinary magnification. A CNN was then built using images classified into seven sites of the stomach (cardia, fundus, body, angular incisure, vestibular part, pyloric antrum, and pylorus; see FIG. 2).

[Preparation of Verification Data Set]

Figure 3:
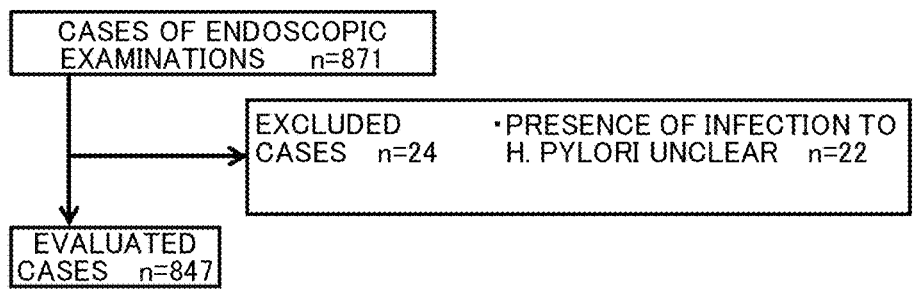
FIG. 3 is a view illustrating a selection of patients for a verification data set for building a CNN according to a first embodiment.

A verification data set was prepared in order to evaluate the accuracies of diagnoses made by the CNN according to the first embodiment, having been built using the training data set described above, and diagnoses made by endoscopy physicians. From the image data of 871 patients who received endoscopic examinations in the clinic to which one of the inventors of the present invention belongs, within a period between May and June in 2017, the image data of 22 patients whose infection to H. pylori was unclear and of 2 patients who had received gastrectomy were excluded. The final verification data set included 23,699 images collected from 847 patients in total (70 patients who were H. pylori positive, 493 patients who were H. pylori negative, and 284 patients who were H. pylori eradicated) (see FIG. 3).

The demographic features of these patients, and the features of the images are indicated in Table 1.

TABLE 1

| Characteristics | | Training data set | Verification data set |
|---|---|---|---|
| Number of images | | 98,564 | 23,699 |
| Number of endoscopy doctors | | 33 | 13 |
| Number of patients | | 5236 | 847 |
| Age of patients (SD (years old)) | | 52.7 (13.2) | 50.4 (11.2) |
| Sex of patients | Male (%) | 480 (45) | 168 (43) |
| | Female (%) | 598 (55) | 226 (57) |
| H. pylori clinical diagnosis Result(%) | Positive | 742 (14) | 70 (8) |
| | Negative | 3,649 (70) | 493 (58) |
| | Eradicated | 845 (16) | 284 (34) |

SD: Standard Deviation 23,699

The clinical diagnoses were made by coproantibody test for 264 patients (31%), and using the anti-H. pylori IgG level in the urine for 126 patients (15%). The cases of 63 patients (7%) were used for a plurality of diagnosis tests. There was no redundancy between the training data set and the verification data set.

[Training/Verification Algorithm]

To build an AI-based diagnostic system, a convolutional neural network (CNN) architecture with 22 layers was built with GoogLeNet (https://arxiv.org/abs/1409.4842), using Caffe framework first developed by the Berkeley Vision and Learning Center (BVLC), as the infrastructure for the development of a leading-edge deep learning neural network developed by Szegedy et al.

Figure 4:
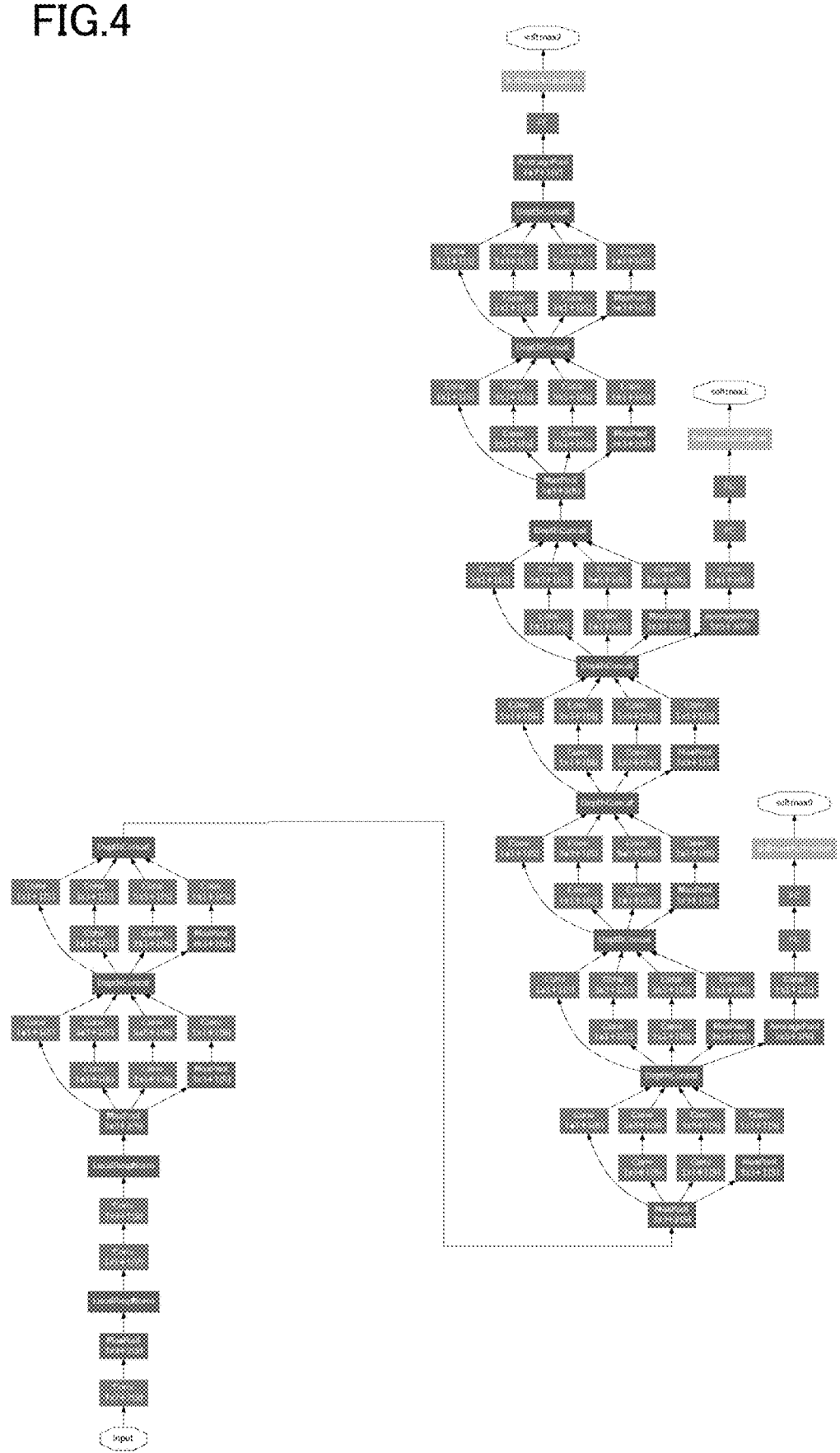
FIG. 4 is a conceptual schematic view illustrating an operation of GoogLeNet.

As illustrated in FIG. 4, the CNN used in the first embodiment was trained with backpropagation. Each layer in the CNN was probabilistically optimized with AdaDelta (https://arxiv.org/abs/1212.5701), at a global learning rate of 0.005. In order to ensure the compatibility with GoogLeNet, all of the images were resized to 244×244 pixels. A trained model trained with the features of natural images in ImageNet was used as the initial values at the time of the start of the training. ImageNet (http://www.image-net.org/) is a database having a collection of over 14 million images at the beginning of 2017. This training technique is referred to as transfer learning, and has been recognized to be effective even when the supervisor data is small in number. In the CNN according to the first embodiment, INTEL Core i7-7700K was used as the CPU, and NVIDEA's GeForce GTX 1070 was used as the graphics processing unit (GPU).

[Evaluation Algorithm]

The trained/verified CNN according to the first embodiment outputs a probability score (PS) within a range between 0 and 1, as diagnosis results for H. pylori positive, H. pylori negative, and H. pylori eradicated, for the input images. Denoting the PS value for H. pylori positive as Pp, denoting the PS value for the H. pylori negative as Pn, and denoting the PS value for the H. pylori eradicated as Pe, $Pp+Pn+Pe=1$ is established. A value with the maximum value among these three probability scores was selected as the seemingly most reliable "diagnosis made by the CNN".

To ensure the anonymity of the patients, the entire patient information was deleted before the data analysis. This research was approved by the Japan Medical Association Ethical Review Board (ID JMA-IIA00283), and was implemented under the Declaration of Helsinki.

Relations between the diagnosis results measured by the CNN according to the first embodiment, and the diagnosis results achieved by the clinical examinations are summarized in Table 2.

TABLE 2

| | | Symptoms confirmed in clinical examinations | | | |
|---|---|---|---|---|---|
| | | Negative | Positive | Eradicated | Total |
| CNN diagnoses | All images negative | 466 (71%) | 22 (3%) | 167 (25%) | 655 |
| | At least one image positive or eradicated | 27 (14%) | 48 (25%) | 117 (61%) | 192 |
| | At least one image eradicated | 16 (13%) | 20 (17%) | 83 (70%) | 119 |

Among the 23,699 images in total, the CNN made a diagnosis of 418 images as *H. pylori* positive, 23,034 images as *H. pylori* negative, and diagnosed 247 images as *H. pylori* eradicated. Among the 655 patients for which all of the images were diagnosed as *H. pylori* negative by the CNN, 466 patients (71%) were diagnosed in the clinical examinations as *H. pylori* negative in the same manner 22 patients (3%) were diagnosed as *H. pylori* positive, and 167 patients (25%) were diagnosed as *H. pylori* eradicated.

Furthermore, among the 192 patients having at least one of their images diagnosed by the CNN as "*H. pylori* positive or eradicated", in the clinical examinations, 48 patients (25%) were diagnosed as *H. pylori* positive, and 117 patients (61%) were diagnosed as *H. pylori* eradicated. Total of 165 patients (86%) were diagnosed as "*H. pylori* positive or eradicated" in the same manner, but 27 patients (14%) were diagnosed as *H. pylori* negative. Among the 119 patients having at least one of their images diagnosed by the CNN as *H. pylori* eradicated, 83 patients (70%) were diagnosed in the clinical examinations as *H. pylori* eradicated, in the same manner, 16 patients (13%) were diagnosed as *H. pylori* negative, and 20 patients (17%) were diagnosed as *H. pylori* positive. The time required for the CNN to diagnose the 23,669 images was 261 seconds.

The following is clear from the results indicated in Table 2. In other words, when a CNN is used in making a diagnosis about the conditions of *H. pylori* infection from a gastroscopic image, it is clear that it is useful to extract the cases of "*H. pylori* positive or eradicated" in a shorter time period by building a training/verification data set for building the CNN, by including not only the images diagnosed as *H. pylori* positive and as negative, but also by including those diagnosed as *H. pylori* eradicated in the clinical examinations. Furthermore, the screening system based on the CNN has a sufficient sensitivity and the degree of specificity to be deployed for clinical practice, and it is suggested that this system can greatly reduce the burden of the work performed by the endoscopy specialists who perform screening of the images (test data) captured during endoscopic examinations.

With the CNN according to the first embodiment, it is possible to reduce the time required for screening the *H. pylori* infection without fatigue, and it becomes possible to acquire report results immediately after the endoscopic examination. In this manner, it is possible to reduce the burden on endoscopy physicians in diagnosing the *H. pylori* infection and the medical care expenditures, both of which are big issues needing to be addressed worldwide. Furthermore, with the diagnoses of *H. pylori* using the CNN according to the first embodiment, because the results can be acquired immediately once the endoscopic image is input, it is possible to provide completely "online" assistance to the diagnoses of *H. pylori*, and therefore, it is possible to solve the problem of heterogeneity of the distribution of the doctors across the regions, by providing what is called "remote medical care".

In Japan, there are many cases of *H. pylori* infection, particularly among the elderly. *H. pylori* eradication therapies for patients with gastritis caused by *H. pylori* infection have come be covered by the Japanese health insurance in February 2013, and actually, the *H. pylori* eradication therapies have come to be widely adopted for patients with *H. pylori* infection. In the mass screening for stomach cancers using endoscopic images started in 2016, an enormous number of endoscopic images was processed, and there has been a demand for a more efficient image screening method. The results acquired in the first embodiment suggest possibilities that, by using this CNN with an enormous number of images in storage, screening of *H. pylori* infection can be assisted greatly without the evaluations of endoscopic examiners, that further tests will lead to more confirmed cases of *H. pylori* infection, and that such cases will be eventually treated with the *H. pylori* eradication. Furthermore, the CNN's diagnostic capability based on the conditions of *H. pylori* infection is improved by adding the classifications of the stomach sites, and it is also possible to improve the diagnostic capability for the stomach cancers by adding information of the conditions of *H. pylori* infection.

Described in the first embodiment is an example in which GoogLeNet was used as the CNN architecture, but CNN architectures are evolving every day, and sometimes better results can be achieved by adopting the latest architecture. Furthermore, while open-source Caffe is used as the deep learning framework, CNTK, TensorFlow, Theano, Torch, MXNet, and the like may also be used. Furthermore, although Adam is used as the optimization technique, it is also possible to use Stochastic Gradient Descent (SGD), MomentumSGV method that is an addition of momentum to the SGD, AdaGrad method, AdaDelta method, NesterovAG method, RMSpropGraves method, and the like, selectively, as appropriate.

As described above, the accuracy of *H. pylori* infection diagnoses made by the CNN according to the first embodiment with the use of the endoscopic images of stomach were comparable to those achieved by endoscopy physicians. Therefore, the CNN according to the first embodiment is useful in selecting patients with *H. pylori* infection based on acquired endoscopic images, for reasons such as screening. Furthermore, because the CNN has been trained with images after the *H. pylori* eradication, it is possible to use the CNN to determine whether the *H. pylori* has been successfully eradicated.

[Diagnostic Assistance System]

A CNN-incorporated computer as a diagnostic assistance system according to the first embodiment basically includes an endoscopic image input unit, a storage unit (a hard disk or a semiconductor memory), an image analyzing device, a determination display device, and a determination output device. The computer may also be directly provided with an endoscopic image capturing device. This computer system may also be installed remotely from an endoscopic examination facility, and operated as a centralized diagnostic assistance system by receiving image information from remote locations, or as a cloud computer system over the Internet.

The storage unit in this computer is provided with a first storage area storing therein a plurality of endoscopic images of a digestive organ acquired in advance from each of a plurality of subjects, a second storage area storing therein final diagnosis results representing the positivity or the negativity to the disease acquired for each of the subjects in advance, and a third storage area storing therein a CNN program. In such a case, because the number of the endoscopic images of the digestive organ acquired in advance from each of the subjects is large, and the data volume is large, and because an enormous number of data processes is performed when the CNN program is run, it is preferable to run the processes in parallel, and to have a large-capacity storage unit.

Because the recent improvement in CPU or GPU performance has been quite prominent, by using a somewhat high-performance commercially available personal computer as the CNN-incorporated computer serving as the diagnostic assistance system used in the first embodiment, it is possible to process 3000 cases or more per hour, as a diagnostic system for gastritis caused by H. pylori infection, and to process a single image in approximately 0.2 seconds. Therefore, by feeding the image data captured by an endoscope to the CNN-incorporated computer used in the first embodiment, it is possible to make a determination of H. pylori infection in real time, and to make remote diagnoses using not only gastroscopic images received from global or remote locations but also using videos. In particular, because the GPUs on the recent computers exhibit extremely high performance, by incorporating the CNN according to the first embodiment, highly accurate image processing can be achieved at a high speed.

Furthermore, the endoscopic image of a digestive organ of a subject, input to the input unit of the CNN-incorporated computer serving as the diagnostic assistance system according to the first embodiment, may be an image captured by an endoscope, an image transmitted over a communication network, or an image recorded in a computer-readable recording medium. In other words, because the CNN-incorporated computer serving as the diagnostic assistance system according to the first embodiment can output probabilities of the positivity and the negativity to the disease in the digestive organ within a short time period, for an input endoscopic image of a digestive organ of a subject, such images can be used regardless of the way in which the endoscopic image of the digestive organ of the subject is input.

As the communication network, the Internet, an intranet, an extranet, a LAN, an ISDN, a VAN, a CATV communication network, a virtual private network, a telephone network, a mobile communication network, a satellite communication network, and the like, which are known, may also be used. Furthermore, as the transmission medium of the communication network, a known wired transmission such as an IEEE1394 serial bus, an USB, a powerline transmission, a cable TV circuit, a telephone network, and an ADSL line, wireless transmission such as via infrared, Bluetooth (registered trademark), and IEEE802.11, or a wireless transmission such as a mobile telephone network, a satellite circuit, and a terrestrial digital network may also be used. Furthermore, as the computer-readable recording medium, it is also possible to use known tapes such as a magnetic tape or a cassette tape, disks including magnetic disks such as a floppy (registered trademark) disk or a hard disk, discs including optical discs such as a compact ROM/an MO/an MD/a digital video disc/a compact disc-R, cards such as an IC card, a memory card, and an optical card, or semiconductor memories such as a mask ROM/an EPROM/an EEPROM/a flash ROM.

Second Embodiment

Figure 5:
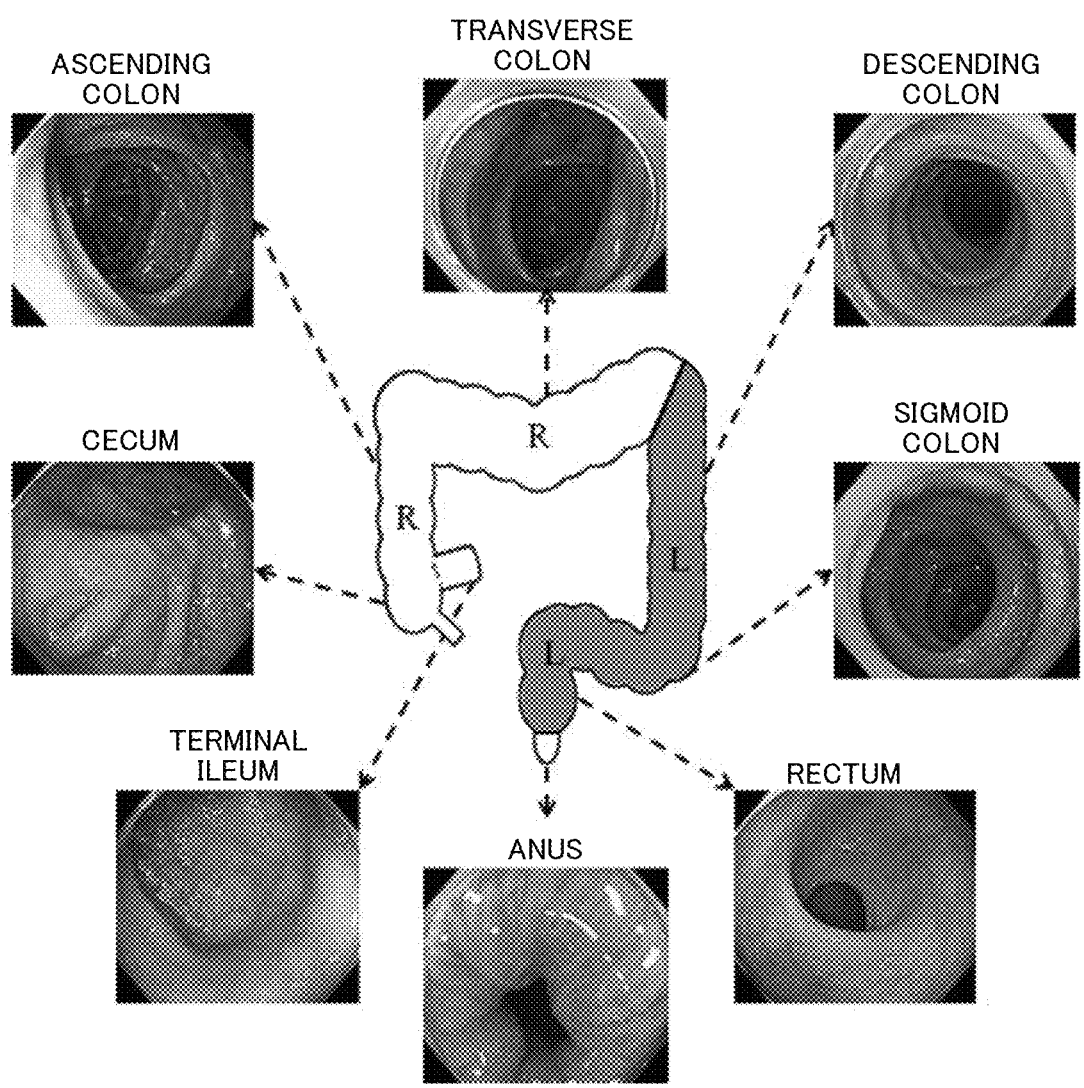
FIG. 5 is a view illustrating main anatomical sites of the large bowel.

In a second embodiment, explained is an example in which the diagnostic assistance method and the diagnostic assistance system for a disease based on an endoscopic image of a digestive organ, the diagnostic assistance program, and the computer-readable recording medium storing therein the diagnostic assistance program according to the present invention are applied to classifications into sites of the large bowel. The sites of the large bowel include the terminal ileum, the cecum, the ascending colon, the transverse colon, the descending colon, the sigmoid colon, the rectum, and the anus. These main anatomical classifications of the large bowel are illustrated in FIG. 5. In the second embodiment, the CNN was trained and verified so as to make the CNN capable of automatically distinguishing the images of these sites.

Clinical data of patients who received total colonoscopy (CS) within a period between January 2017 and November 2017 in the clinic to which one of the inventors of the present invention belongs, was reviewed retrospectively. The reasons for performing the CS included abdominal pains, diarrhea, positive fecal immunochemical tests, as a follow-up of the past CS in the same clinic, and as mere screening. In order to correctly identify the anatomical sites of the large bowel and rectum, only the images of a normal large bowel and rectum filled with a sufficient amount of air, with the sites having been identified were used. A major portion of excluded images included those with a colorectal polyp, a cancer, and a biopsy scar, for example, and those with severe inflammation or bleeding were also excluded. Only white light images or emphasized images at an ordinary magnification were included.

The images captured in the CS were captured using a standard colonoscope (EVIS LUCERA ELITE, CF TYPE H260AL/I, PCF TYPE Q260AI, Q260AZI, H290I, and H290ZI, Olympus Medical Systems Corp., Tokyo, Japan) Images of the ileum, the cecum, the ascending colon, the transverse colon, the descending colon, the sigmoid colon, the rectum, and the anus were captured during the course of CS, and 24 images were acquired for each part on the average, during the CS.

In order to train/verify the CNN, all pieces of the patient information associated with the images was anonymized, before the algorithm was developed. It was also ensured that none of the endoscopy physicians involved with the CNN according to the second embodiment had any access to any identifiable patient information. Because this training/verification of the CNN was a retrospective study using the anonymized data, an opt-out approach was used for the consent from the patients. This study was approved by the Japan Medical Association Ethical Review Board (ID: JMA-IIA00283).

Figure 6:
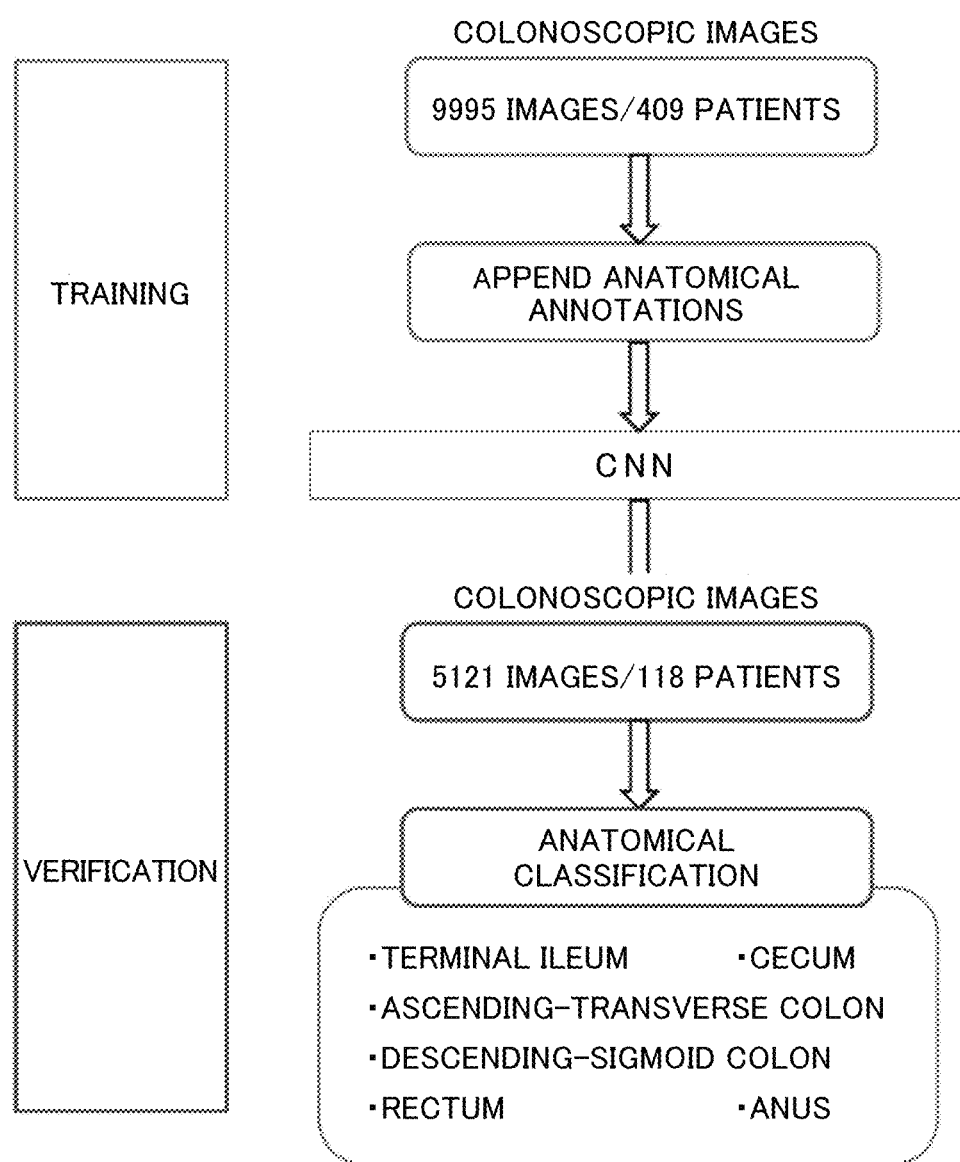
FIG. 6 is a schematic view of a flowchart for building a CNN system according to a second embodiment.

An overview of a flowchart for the CNN system according to the second embodiment is illustrated in FIG. 6. In this flowchart, the images were classified by endoscopy specialists in order to train/verify the CNN into seven categories of the terminal ileum, the cecum, the ascending and transverse colons, the descending and sigmoid colons, the rectums, the anus, and unclassifiable. All of the training/verification images had their classifications checked by at least two endoscopy specialists, before the CNN was trained/verified. The training/verification data set was classified into six categories of the terminal ileum, the cecum, the ascending and transverse colons, the descending and sigmoid colons, the rectum, and the anus. The training/verification data set did not include any unclassifiable images.

Conventionally, 5,000 or less images of the image data required to build an AI system for colorectal polyps were used in the training. Therefore, in order to ensure a sufficient amount of data, an aim was set to build the CNN system according to the second embodiment, using about 10,000 images. As training images, 9995 images of 409 patients collected within a period between January 2017 and March 2017 were prepared, and 5121 images of 118 patients acquired in November 2017 were used as a verification image set (see Table 3). The number of images of each of the anatomical sites in each of these image sets is indicated in Table 4.

TABLE 3

|  | Training data set | Verification data set |
|---|---|---|
| Age | 49.7 ± 10.8 | 51.0 ± 11.0 |
| Number of Males (%) | 180 (44.0) | 39 (33.0) |
| Number of Patients (Number of Images) | 409 (9,995) | 118 (5,121) |

TABLE 4

| Classification | Sub-classification | Number of images in training/verification data set (%) | Number of images in test data set (%) |
|---|---|---|---|
| Terminal ileum |  | 652 (6.5) | 209 (4.1) |
| Cecum | Right colon | 1,048 (10.5) | 423 (8.3) |
| Ascending-transverse colon |  | 2,376 (23.8) | 1,742 (34.0) |
| Descending-sigmoid colon | Left colon | 3,535 (35.4) | 2,081 (40.6) |
| Rectum |  | 1,037 (10.4) | 467 (9.1) |
| Anus |  | 970 (9.7) | 199 (3.9) |
| Unclear |  | 377 (3.8) | 0 (0) |
| Total |  | 9,995 (100) | 5,121 (100) |

All of the images in the training/verification data set acquired in the manner described above in the second embodiment were resized to 244×244 pixels to ensure compatibility with GoogLeNet. The CNN system used in the second embodiment was trained using the same approach as that used for the CNN system according to the first embodiment.

The CNN system according to the second embodiment outputs probability scores (PS) for the respective sites in the training/verification images. The probability score takes a value within a range of 0 to 1 (0 to 100%), and represents the probability at which the image belongs to a corresponding site of the large bowel. The CNN calculates, for each of the images, a probability score for each of the seven sites (the terminal ileum, the cecum, the ascending and transverse colons, the descending and sigmoid colons, the rectum, the anus, and the unclassifiable). The anatomical site with the highest probability score is assigned as the site of the image. The sites of the large bowel are sometimes classified into four sites of the terminal ileum, the right colon, the left colon, and the anus, by putting the cecum, the ascending colon, and the transverse colon into the right colon, and putting the descending colon, the sigmoid colon, and the rectum into the left colon, based on the similarity of their tissues.

For example, the colonoscopic image on the left side of FIG. 7 is an example of an image of the ascending-transverse colon, in which the CNN determined a probability score of 95% for the ascending-transverse colon, and also determined a probability score of 5% for the descending-sigmoid colon. As a result, the CNN assigns the colonoscopic image on the left in FIG. 7, to the ascending-transverse colon.

The main objective of the CNN according to the second embodiment is to acquire the sensitivity and the degree of specificity of the anatomical classifications of the colonoscopic images, by the CNN. A receiver operating characteristic (ROC) curve is plotted for each of the sites, and the area under the curve (AUC), under the ROC curve, was calculated using GraphPad Prism 7 (GraphPad software Inc., California, U.S.A.). The ROC curves corresponding to the respective sites of the large bowel, created by the CNN according to the second embodiment, are illustrated in FIG. 8. FIGS. 8A to 8F are views illustrating the ROC curves for the terminal ileum, the cecum, the ascending colon, the descending colon, the sigmoid colon, the rectum, and the anus, respectively.

The CNN system built in the second embodiment correctly recognized 66.6% of the images (3,410/5,121 images) of the verification data set. Table 5 indicates the correct recognition ratios based on the probability scores assigned to the images by the CNN.

TABLE 5

| Probability score | Number of correct determinations | Number of all images | Correctness |
|---|---|---|---|
| >99% | 465 (14) | 507 (10) | 91.7% |
| >90% | 1,039 (30) | 1,296 (25) | 80.2% |
| >70% | 1,009 (30) | 1,549 (30) | 65.1% |
| >50% | 761 (22) | 1,397 (27) | 54.5% |
| ≤50% | 136 (4) | 372 (7) | 36.6% |
| Total | 3,410 (100) | 5,121 (100) | 66.6%* |

*Average

The CNN system assigned the probability scores higher than 99% to 10% (507 images) of the entire images (5,121 images), and 465 images (14% of those correctly classified) of them were those correctly classified by the clinical diagnoses. Therefore, the correctness was 91.7%.

In the same manner, the CNN system assigned the probability scores higher than 90% and equal to or less than 99% to 25% (1,296 images) of the entire images, and 1,039 (30% of those correctly classified) of the images corresponded to those classified correctly by the clinical diagnoses. Therefore, the correctness was 80.2%. In the same manner, the CNN system assigned the probability scores higher than 70% and equal to or less than 90% to 30% (1,549) of the entire images, and 1,009 (30% of those correctly classified) of them were those classified correctly by the clinical diagnosis. Therefore, the correctness was 65.1%.

In the same manner, the CNN system assigned the probability scores higher than 50% and equal to or less than 70% to 27% (1,397 images) of the entire images, and 761 (22% of those correctly classified) of the images corresponded to those classified correctly by the clinical diagnoses. Therefore, the correctness was 54.5%. Furthermore, the CNN system assigned the probability scores equal to or lower than 50% to 7% (372 images) of the entire images, and 136 (4% of those correctly classified) of the images corresponded to those classified correctly by the clinical diagnoses. Therefore, the correctness was 36.6%.

Table 6 indicates the CNN output distribution for each of the anatomical sites classified by the clinical diagnoses. In this table, there is no image classified into "unclassifiable".

TABLE 6

| CNN output | Terminal ileum n = 209 (%) | Cecum (n = 423) (%) | Ascending-transverse colon (n = 1,742) (%) | Descending-sigmoid colon (n = 2,081) (%) | Rectum (n = 467) (%) | Anus (n = 199) (%) |
| --- | --- | --- | --- | --- | --- | --- |
| Terminal ileum | 145 (69) | 13 (3) | 4 (0) | 11 (1) | 6 (1) | 0 (0) |
| Cecum | 9 (4) | 211 (50) | 64 (4) | 7 (0) | 4 (1) | 0 (0) |
| Ascending-transverse colon | 6 (3) | 89 (21) | 891 (51) | 108 (5) | 6 (1) | 1 (1) |
| Descending-sigmoid colon | 40 (19) | 97 (23) | 775 (44) | 1,872 (90) | 265 (57) | 13 (7) |
| Rectum | 1 (0) | 4 (1) | 1 (0) | 78 (4) | 109 (23) | 3 (2) |
| Anus | 8 (4) | 9 (2) | 7 (0) | 5 (0) | 77 (16) | 182 (91) |
| Unclear | 0 (0) | 0 (0) | 0 (0) | 0 (0) | 0 (0) | 0 (0) |
| Sensitivity | 69.4 | 49.8 | 51.1 | 90.0 | 23.3 | 91.4 |
| Degree of specificity | 99.3 | 98.2 | 93.8 | 69.9 | 98.1 | 97.8 |

For the CNN built in the second embodiment, the sensitivity at which the images were recognized was the highest for the anus at 91.4%, the descending colon and the sigmoid colon were the second highest at 90.0%, the sensitivity for the terminal ileum was 69.4%, the sensitivity for the ascending colon and the transverse colon was 51.1%, and the sensitivity for the cecum was 49.8%, but the sensitivity for the rectum was the lowest at 23.3%. The degree of specificity for each of the anatomical sites was 90% or higher except for that of the sites of the descending colon and the sigmoid colon (60.9%). The CNN built in the second embodiment recognized images having an AUC exceeding 0.8, for all of the anatomical sites.

Table 7 indicates an output distribution of the CNN built in the second embodiment, for the terminal ileum, the right colon, the left colon, and the anus, by representing the cecum, the ascending colon, and the transverse colon as the "right colon", and representing the descending colon, the sigmoid colon, and the rectum as the "left colon". For the left colon, the CNN exhibited a high sensitivity of 91.2% and a relatively low specificity of 63.%, but exhibited reversed results for the terminal ileum, the right colon, and the anus.

TABLE 7

| CNN output | Terminal ileum n = 209 (%) | Right colon (n = 2,165) (%) | Left colon (n = 2,548) (%) | Anus (n = 199) (%) |
| --- | --- | --- | --- | --- |
| Terminal ileum | 145 (69) | 17 (1) | 17 (1) | 0 (0) |
| Right colon | 15 (7) | 1,255 (58) | 125 (5) | 1 (1) |
| Left colon | 41 (20) | 877 (41) | 2,324 (91) | 16 (8) |
| Anus | 8 (4) | 16 (1) | 82 (3) | 182 (91) |
| Sensitivity | 69.4 | 58.0 | 91.2 | 91.5 |
| Degree of specificity | 99.3 | 95.2 | 63.7 | 97.8 |

The sensitivity and the degree of specificity were calculated for each of the anatomical sites, in each of the four sections of specific probability scores, that is, 70%≥PS>60%, 80%≥PS>70%, 90%≥PS>80%, and PS>90%. The calculation results are indicated in Table 8.

TABLE 8

| Probability Score (PS) | | Terminal ileum | Cecum | Ascending-transverse colon | Descending-sigmoid colon | Rectum | Anus |
| --- | --- | --- | --- | --- | --- | --- | --- |
| PS > 60 | Sensitivity | 80.1 | 62.7 | 52.5 | 94.7 | 18.1 | 94.1 |
| | Specificity | 99.6 | 98.9 | 97.0 | 61.6 | 89.9 | 98.0 |
| PS > 70 | Sensitivity | 81.8 | 67.6 | 53.6 | 96.2 | 15.1 | 95.1 |
| | Specificity | 99.7 | 99.0 | 98.0 | 63.0 | 99.1 | 97.9 |
| PS > 80 | Sensitivity | 88.2 | 77.0 | 55.6 | 97.6 | 12.4 | 96.6 |
| | Specificity | 99.8 | 99.2 | 99.0 | 66.8 | 99.5 | 97.9 |
| PS > 90 | Sensitivity | 92.2 | 82.7 | 56.5 | 99.1 | 8.2 | 97.0 |
| | Specificity | 99.8 | 99.3 | 99.5 | 72.9 | 99.9 | 97.5 |

According to the results indicated in Table 8, for all of the probability scores, when the probability score was higher, the sensitivity and the degree of specificity were higher, in all of the sites excluding the rectum. However, in the rectum, although the degree of specificity was higher when the probability score was higher, the sensitivity did not match the trend of the probability scores.

Figure 9A:
FIG. 9A is a view illustrating an image correctly recognized as the anus and probability scores corresponding to respective sites.
Figure 9B:
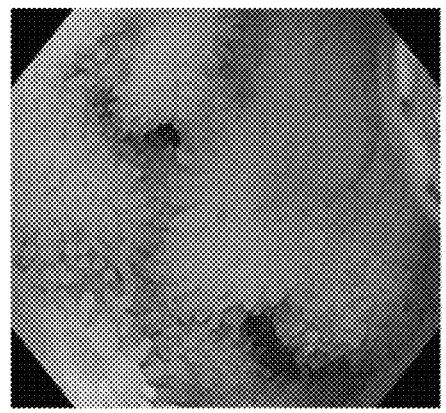
FIG. 9B is a view illustrating an image of the terminal ileum, erroneously recognized as the anus, and probability scores corresponding to the respective sites.
Figure 10A:
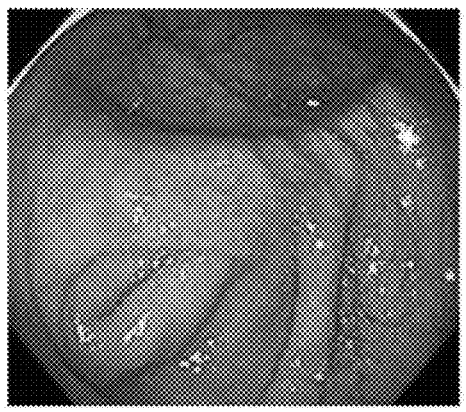
FIG. 10A is a view illustrating an image correctly recognized as the cecum, and probability scores corresponding to the respective sites.
Figure 10B:
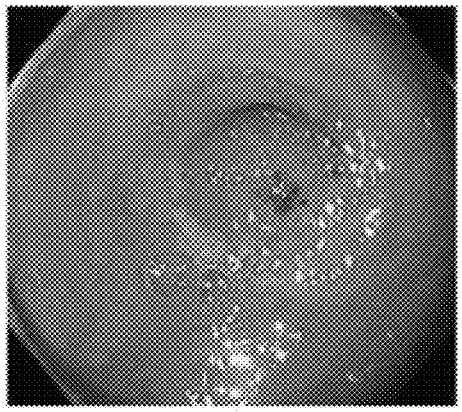
FIG. 10B is a view illustrating an image of the cecum, erroneously recognized as the terminal ileum, and probability scores corresponding to the respective sites.

Review was then conducted on 1,711 images (subtracting the number of correctly determined images from the total number of images=5,121-3,410=1,711, see Table 5) erroneously recognized by the CNN according to the second embodiment. The CNN system according to the second embodiment erroneously recognized 17.5% of the entire images (299/1,711), and their probability scores were 0.9 or higher. FIGS. 9 and 10 illustrate typical examples of the images erroneously recognized by the CNN according to the second embodiment. FIG. 9A is an example of an endoscopic image recognized correctly as the anus, and FIG. 9B illustrates an image of terminal the ileum erroneously recognized as the anus. The contour of the lumen in FIG. 9B was similar to the contour of the anus. FIG. 10A is an example of an endoscopic image recognized correctly as the cecum, and FIG. 10B is an example of an image of the cecum erroneously recognized as the terminal ileum. In FIG. 10A, the appendix cavity is visible as one of the features of the cecum, but in FIG. 10B, the cecum was erroneously recognized as the terminal ileum.

As described above, in the second embodiment, a CNN system was build based on the 9995 colonoscopic images of the 409 patients. The CNN system was caused to identify the anatomical sites using an independent large-scale verification data set, and this CNN system exhibited clinically useful performance. This CNN system succeeded in recognizing the images of the colon at an accuracy of 60% or higher. Therefore, it is expected that this system will serve as the foundation for the development of AI systems for colonoscopy in the near future.

In order to develop an AI system for colon diseases, the first important factor is the capability for efficiently recognizing the anatomical sites in the image. Conventionally, an AI system for recognizing colon polyps has been known, but its sensitivity was within a range of 79% and 98.7%, and its degree of specificity was within a range of 74.1% and 98.5%. The conventional systems do not have capability for recognizing the anatomical site of the polyp. It is well-known that the frequency of polyp or colorectal cancer occurrence differs depending on the anatomical sites of the colon. If the CNN system according to the second embodiment can change the sensitivity at which a colon lesion is detected based on the anatomical site, it is possible to develop a more effective AI system.

In the CNN built in the second embodiment, the accuracy varied depending on the value of the probability score. Generally, because images with higher probability scores are recognized at a higher accuracy, the CNN is enabled to function better by limiting the images only to those with higher probability scores. To realize a clinically useful application, appropriate probability scores are required to achieve more reliable recognition results.

The results achieved by the CNN built in the second embodiment was not any better than the previous reports made by the inventors of the present invention who built a CNN system capable of classifying gastrointestinal images. The conventional sensitivity and the degree of specificity for recognizing anatomical sites of gastrointestinal tract were 93.9% and 100% for the larynx, 95.8% and 99.7% for the esophagus, 98.9% and 93.0% for the stomach, and 87.0% and 99.2% for the duodenum.

However, even for clinicians, it is difficult to recognize the anatomical sites correctly in the colonoscopic image, at the same level as for the anatomical sites of the gastrointestinal endoscopic image. For example, clinicians are sometimes not able to distinguish an image of the ascending-transverse colon from an image of the descending-sigmoid colon. In particular, images with a margin in sites are difficult to recognize. Furthermore, clinicians can usually recognize which site a colonoscopic image represents by considering the successive order of the images, or a relation of an image with a previous or subsequent image in the clinical setting. Because a 66-% accuracy achieved by the CNN based on one image can be improved by integrating a relation of the image with a previous or subsequent image in the manner described above, which cannot be underestimated.

The sensitivity and the specificity of the CNN system built in the second embodiment vary depending on anatomical sites. For the descending colon-sigmoid colon site, the CNN exhibited a high sensitivity of 90% or higher, but exhibited the lowest specificity of 69.9%. By contrasts, for the terminal ileum, the cecum, the ascending colon-transverse colon, and the rectum, the CNN exhibited high specificities but exhibited low sensitivities of 23.3 to 69.4%. Furthermore, the CNN according to the second embodiment recognized the anus at a high sensitivity and specificity of 90% or higher. Interestingly, the sensitivity at which the rectum is recognized dropped when the sensitivity was calculated from an image with a high probability score.

The CNN according to the second embodiment failed to make a correct output reliably for rectum images, and recognized the rectum images as the descending-sigmoid colon. It is assumed that the reason why the rectum was recognized at low sensitivity is that the rectum has no characteristic portion. However, with the CNN according to the second embodiment, although the terminal ileum and the cecum had characteristic portions such as an ileocecal valve and an appendix orifice, respectively, the recognition sensitivities remained relatively low. The reason why such results were acquired can be explained by the fact that the CNN system according to the second embodiment was not able to recognize the characteristic portions belonging to the respective sites. The reason is that the CNN system according to the second embodiment can recognize an image based only on the entire structure in the image, and merely classifies the images into respective sites without being trained with the characteristic portions based on the sites represented in the images. The recognition accuracy of the sites will be improved if the CNN system according to the second embodiment can be trained with typical portions of the image.

In other words, it becomes difficult to capture the shape of a lumen if the endoscope is moved closer to the surface of the site, or when the lumen is not sufficiently filled with the air. Because the epithelia of the esophagus, the stomach, and the duodenum in the images of the esophagus, the stomach, and the duodenum are different from one another, it is necessary to recognize images based on the microstructure of the surface. For example, in the stomach, the epithelium is classified differently depending on the anatomical sites. For example, pyloric glands are distributed across the gastric pylorus, and gastric fundic glands exist in another area.

By contrast, the cecum, the ascending colon, the transverse colon, the descending colon, the sigmoid colon, and the rectum all have microstructures the patterns of which are almost the same. Therefore, it is inefficient to train the CNN with the surface microstructures so as to enable the CNN to distinguish colorectal images. However, it is effective to train the CNN with the surface microstructure in order to enable the CNN system according to the second embodiment to recognize the terminal ileum or the anus.

Furthermore, in the CNN system according to the second embodiment, in order to improve the capability for aligning the image to the exact position, the colonoscopy may be combined with another modality for capturing medical images, such as an X-ray computed tomography (CT) device, an ultrasonic computer tomography (USCT) device, and a magnetic resonance imaging (MRI) device capable of displaying three-dimensional information such as a computer tomographic image or a fluoroscopic image. When images with such modalities can be used for the training data set, the CNN can recognize the position of the colonoscopic images more correctly.

The capability for automatically recognizing the anatomical sites of the colon will have a great impact on the diagnoses as well as on the treatments. Firstly, the position where the colon disease is located is recognized. For example, in the treatment of ulcerative colitis, treatment can be provided or an appropriate type of drug can be administered, based on the site where the colitis is present. Furthermore, in relation to the colorectal cancer, the anatomical site where the cancer is located is important information for surgery.

Secondly, the information related to anatomical sites of the colon is useful for exact examination in a process between inserting and discharging a colonoscope. In particular, in order for a medical intern who are in the process of training or a physician at the first contact to complete the insertion of an endoscope scope, one of the most difficult tasks is to recognize where the endoscope scope is inserted. If the CNN enables them to objectively recognize the position where the endoscope scope is located, such information is useful for a medical intern who are in the process of training or a physician at first contact to insert the colonoscope. If the function for recognizing the anatomical sites is provided in video images, the time and the difficulty for completing the insertion of the colonoscope can be reduced.

The CNN system according to the second embodiment has some limitations that require some consideration. Firstly, the correctness is dependent on the ability or the skill of the specialists who classified the verification images. The ability of the specialist who recognizes the anatomical sites from the colonoscopic image is dependent on endoscopic experiences or skills, such as the number of times of the colonoscopy, the training period, and an endoscopy qualification. In the CNN system according to the second embodiment, because one physician is assigned to the verification data set, there is a possibility that the verification data set contains images that are erroneously classified. To assign the images correctly, it is necessary to have a plurality of physicians classify all of the images.

Secondly, in the CNN system according to the second embodiment, all of the images were acquired at a single facility. The number of colonoscopic images of the sites, the amount of the air filled in the lumen, or the angle of the image may differ depending on the policy of the practitioner or the facility.

Finally, in building the CNN for the colonoscopy according to the second embodiment, a larger number of images was used for both of the training data and the verification data, than that having been conventionally used. In order to build a more reliable CNN, it is more preferable to use a larger number of images. Generally, in order to build a CNN system capable of distinguishing images correctly based on the characteristics, 10,000 or more images might be required. It is also required to prepare a larger number of training data sets assigned by a plurality of physicians, from a plurality of facilities.

As described above, in the second embodiment, a clinically appropriate performance of a newly built CNN system has been clarified, from the viewpoint of the anatomical sites in the colonoscopic images. This will be the first step for building a CNN system that is capable of detecting a colon disease more easily.

Third Embodiment

In a third embodiment, a diagnostic assistance method, a diagnostic assistance system, a diagnostic assistance program, and a computer-readable recording medium storing therein the diagnostic assistance program for a disease in a small bowel based on a wireless capsule endoscope (WCE) image will now be explained. In the third embodiment, because the distinction between erosion and ulcer was difficult, the erosion and ulcer are collectively described as "erosion/ulcer". In other words, the term "erosion/ulcer" herein is used to mean not only "erosion", "ulcer", and "erosion and ulcer", but also "not clear whether it is erosion or ulcer, but at least not a normal mucous membrane".

[About Data Set]

As the training data set, 5360 images of erosion/ulcer in the small bowel were collected from 115 patients who received WCE within a period between October 2009 and December 2014 in the clinic to which one of the inventors of the present invention belongs. Furthermore, for the verification of the CNN, 10,440 independent images were prepared from 65 patients within a period between January 2015 and January 2018, and such images were used for a verification data set. In this verification data set, 440 images from 45 patients included erosion/ulcer in the small bowel, and 10,000 image from 20 patients were diagnosed to be a normal mucous membrane of the small bowel by three endoscopy specialists. The WCE was performed using a Pillcam (registered trademark) SB2 or SB3WCE (Given Imaging, Yoqneam, Israel).

Figure 11:
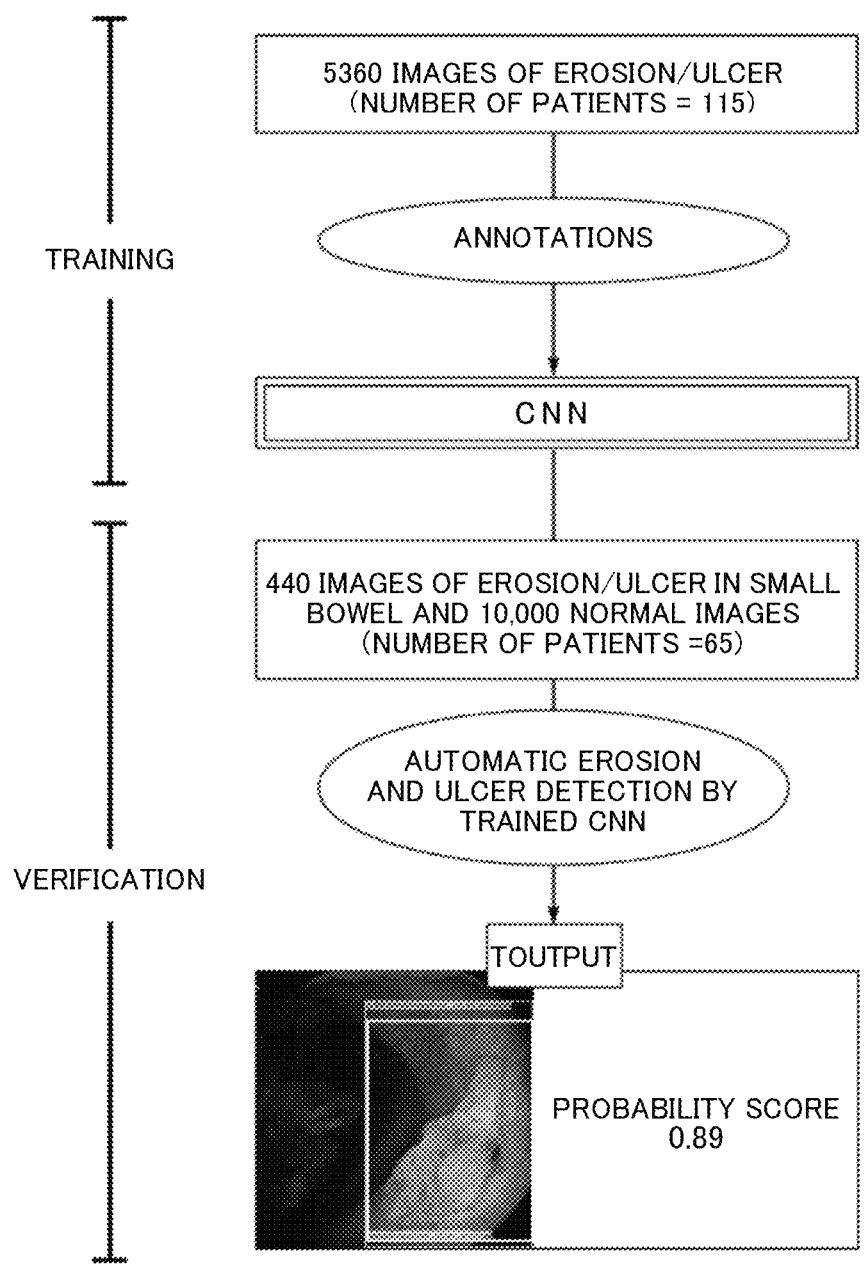
FIG. 11 is a schematic view illustrating a flowchart for building a CNN system according to a third embodiment.

In order to train/verify the CNN, all pieces of the patient information associated with the images was anonymized, before the algorithm was developed. It was also ensured that none of the endoscopy physicians involved with the CNN according to the first embodiment had any access to any identifiable patient information. Because this training/verification of the CNN was a retrospective study using the anonymized data, an opt-out approach was used for the consent from the patients. This study was approved by the Ethics Committee of the University of Tokyo (No. 11931) and the Japan Medical Association Ethical Review Board (ID JMA-IIA00283). An overview of a flowchart for the CNN system according to the third embodiment is illustrated in FIG. 11.

Indications for the WCE were mainly gastrointestinal bleeding of an unknown cause, and others included cases in which abnormality in the small bowel was observed in an image using another medical device, abdominal pains, a follow-up of a past small bowel case, or a referral concerning screening for diarrhea from a primary care physician. The most frequent cause was nonsteroidal anti-inflammatory, and an inflammatory bowel disease came to the second. Other main causes were a malignant tumor in the small bowel, and anastomotic ulcer. However, there were many cases the cause of which could not be identified. The patient characteristics of the data set used for the training and the verification of CNN are indicated in Table 9.

TABLE 9

| Characteristics, number (%) | Training Data Set (n = 115) | Verification Data Set | |
|---|---|---|---|
| | | Erosion, ulcer (n = 45) | Normal (n = 20) |
| Number of Images | 5360 | 440 | 10,000 |
| Average Age (±SD) | 63 ± 16 | 59 ± 21 | 52 ± 12 |
| Sex (male) | 62 (54) | 28 (62) | 12 (60) |
| Reason for receiving WCE | | | |
| Gastrointestinal bleeding of unknown cause | 78 (69) | 29 (64) | 12 (60) |
| Abnormality in small bowel image with another medical device | 12 (10) | 2 (4) | 2 (10) |
| Abdominal pains | 8 (7) | 1 (2) | 3 (15) |
| Follow-ups | 6 (5) | 3 (7) | 0 (0) |
| Diarrhea | 4 (3) | 4 (9) | 1 (5) |
| Screening | 3 (3) | 1 (2) | 1 (5) |
| Crohn's disease | 2 (2) | 3 (7) | 0 (0) |
| Lymphoma | 2 (2) | 2 (4) | 1 (5) |
| Number of lesions | | | |
| One | 40 (35) | 12 (27) | — |
| More than one | 75 (65) | 33 (73) | — |
| Site of lesion | | | |
| Jejunum | 32 (28) | 13 (29) | — |
| Ileum | 47 (41) | 13 (29) | — |
| Diffuse lesion | 36 (31) | 19 (42) | — |
| Cause of disease | | | |
| Nonsteroidal anti-inflammatory drug | 30 (26) | — | — |
| inflammatory bowel disease | 10 (9) | 5 (11) | — |
| malignant tumor in small bowel* | 8 (7) | 2 (4) | — |
| anastomotic ulcer | 7 (6) | 2 (4) | — |
| ischemic enteritis | 2 (2) | 2 (4) | — |
| Meckel's diverticulum | 2 (2) | 0 (0) | — |
| Radiation enteritis | 1 (1) | 0 (0) | — |
| Infectious enteritis | 0 (0) | 1 (2) | — |
| Other cases | 3 (3)** | 3 (7)*** | — |
| Unknown | 52 (45) | 14 (31) | — |

*Including small intestine cancer and lymphoma
**Scar (n = 1) and damages caused by double-balloon endoscope (n = 2)
***graft-versus-host disease (GVHD) (n = 3)

[Training/Verification Algorithm]

In order to build an AI-based diagnostic system, a deep neural network architecture referred to as Single Shot MultiBox Detector (SSD, https://arxiv.org/abs/1512.02325) was used without changing the algorithm. To begin with, two endoscopy specialists manually appended annotations having a rectangular boundary box to all regions of the erosion/ulcer in the images of the training data set. These images were then incorporated into the SSD architecture via the Caffe framework developed first in the Berkeley Vision and Learning Center. The Caffe framework is one of the frameworks that was developed first and is most common and widely used.

The CNN according to the third embodiment was "educated" that the regions inside the boundary box are an erosion/ulcer region, and the other regions are the background. The CNN then extracted specific features of the boundary box region by itself, and "learned" the features of erosion/ulcer through the training data set. All of the layers in the CNN was applied with a probabilistic optimization at a global learning rate of 0.0001. Each of the images was resized to 300×300 pixels. In response, the size of the boundary box was changed, too. These values were set through trial and error to ensure that every piece of data has compatibility with SSD.

[Measurement Results and Statistics]

To begin with, a rectangular boundary box (hereinafter, referred to as a "true box") was manually plotted to all of the erosions/ulcers in the images included in the verification data set, using a thick line. The trained CNN was then caused to plot a rectangular boundary box (hereinafter, referred to as a "CNN box") with a thin line to the region corresponding to the erosion/ulcer detected from the image in the verification data set, and to output a probability score (within the range of 0 and 1) for the erosion/ulcer. When the probability score is higher, it means that the CNN has determines that the region is more likely to include erosion/ulcer.

The inventors of the present invention then evaluated the capability with which the CNN according to the third embodiment determines whether each of the images includes erosion/ulcer. To make this evaluation, the following definitions were used.

1) When the CNN box overlapped with the true box by 80% or higher, the answer was determined to be correct.

2) When there were a plurality of CNN boxes within one image, and at least one of the boxes had correctly detected erosion/ulcer, it was concluded that the image is identified correctly.

The WCE endoscopic image determined to be correct in the manner described above is used as a diagnostic assistance in double-checking captured images in the practice, by assigning the information to the images, or used as a diagnosis assistance by displaying the information in real time as a video, when a WCE endoscopic examination is carried out.

A receiver operating characteristic (ROC) curve was then plotted by changing the cut-off value of the probability scores, and the area under the curve (AUC) was calculated, to evaluate the erosion/ulcer identification performed by the CNN according to the first embodiment. By using various cut-off values of the probability scores including the scores following the Youden index, the sensitivity, the degree of specificity, and the accuracy representing the capability with which the CNN according to the third embodiment detects erosion/ulcer were then calculated. The Youden index is one of the standard methods for determining an optimal cut-off value, calculated with the sensitivity and the degree of specificity, and used to obtain a cut-off value that maximizes the value of "sensitivity+degree of specificity−1". In this example, the data was statistically analyzed using STATA software (version 13; StataCorp, College Station, TX, USA).

The verification data set contained 10,440 images of 65 patients (male=62%, average age=57, standard deviation (SD) age=19). The trained CNN according to the first embodiment required 233 seconds in the evaluation of these images. This is equivalent to a speed of 44.8 images per second. The AUC of the CNN having detected erosion/ulcer was 0.960 (with a 95% confidence interval [CI], 0.950-0.969; see FIG. 12).

According to the Youden index, the optimal cut-off value for the probability score was 0.481, and the region with a probability score of 0.481 was recognized as erosion/ulcer by the CNN. At the cut-off value, the sensitivity, the degree of specificity, and the accuracy of the CNN were 88.2% (95% CI (confidence interval), 84.8 to 91.0%), 90.9% (95% CI, 90.3 to 91.4%), and 90.8% (95% CI, 90.2 to 91.3%) (see Table 10). Table 10 indicates the sensitivity, the degree of specificity, and the accuracy when the cut-off value of the probability scores was increased from 0.2 to 0.9 at an increment of 0.1.

TABLE 10

| Cut-off value (probability score) | Sensitivity (%) | Degree of specificity (%) | Accuracy (%) |
| --- | --- | --- | --- |
| 0.2 | 98.9 | 56.0 | 57.8 |
| 0.3 | 95.9 | 76.7 | 77.5 |
| 0.4 | 91.6 | 86.0 | 86.3 |
| 0.481* | 88.2 | 90.9 | 90.8 |
| 0.5 | 86.8 | 91.7 | 91.5 |
| 0.6 | 81.4 | 94.9 | 94.4 |
| 0.7 | 74.6 | 97.2 | 96.2 |
| 0.8 | 63.6 | 98.6 | 97.1 |
| 0.9 | 45.2 | 99.3 | 97.1 |

*Calculation with Youden index

Relations between the results of erosion/ulcer classification classified in the manner described above by the CNN according to the first embodiment, with a cut-off value of the probability scores=0.481, and the results of erosion/ulcer classification classified by the endoscopy specialists are summarized in Table 11.

TABLE 11

| | | Classification by specialists | | |
| --- | --- | --- | --- | --- |
| | | Erosion/ulcer | Normal | Total |
| Classification by CNN | Erosion/ulcer | 388 | 913 | 1,301 |
| | Normal | 52 | 9,087 | 9,139 |
| | Total | 440 | 10,000 | 10,440 |

Sensitivity = 88.2%
Degree of specificity = 90.9%

Furthermore, FIGS. 13A to 13D illustrate typical regions correctly detected by the CNN, and FIGS. 14A to 14H illustrate typical regions erroneously classified by the CNN. As indicated in Table 12, causes of the false negative images were classified into the following four classes: the boundary was unclear (see FIG. 14A); the color was similar to that of the normal mucous membrane therearound; the size was too small; and the entire picture was not observable (due to the laterality (the affected area is hard to see because the area is located on the side) or the partiality (only partially visible)) (see FIG. 14B).

TABLE 12

| Cause of False Negative (n = 52) | n (%) |
| --- | --- |
| Unclear boundary* | 33 (64) |
| Same color as that of surrounding mucous membrane | 11 (21) |
| Too small | 6 (12) |
| Not entirely observable | 2 (4) |

*Due to darkness, debris, or out of focus

By contrast, the causes of the false positive images were classified into five classes of normal mucous membrane, bubbles (FIG. 14C), fragments (FIG. 14D), vasodilatation (FIG. 14E), and true erosion (FIGS. 14F to 14H), as indicated in Table 13.

TABLE 13

| Cause of false positive (n = 913) | n (%) |
| --- | --- |
| Normal mucous membrane | 347 (38) |
| Bubbles | 228 (25) |
| Debris | 216 (24) |
| Vasodilatation | 119 (13) |
| True erosion** | 3 (0.3) |

Those recognized as erosion by endoscopy specialists after CNN pointed out lesions As described above, with the trained CNN according to the third embodiment, a CNN-based program for automatically detecting erosion and ulcer in WCE images of the small bowel was built, and it became clear that in detection of erosion/ulcer succeeds in independent test images at a high accuracy of 90.8% (AUC, 0.960**).

Fourth Embodiment

In a fourth embodiment, a diagnostic assistance method, a diagnostic assistance system, a diagnostic assistance program, and a computer-readable recording medium storing therein the diagnostic assistance program for diagnosing the invasion depth of squamous cell carcinoma (SCC) using an ordinary endoscope (a non-magnifying endoscope, a non-ME), an endoscopic ultrasonography (EUS), and a magnifying endoscope (ME) will be explained.

To begin with, a relation between an invasion depth of an esophageal SCC and its classification will be explained with reference to FIG. 15. The esophagus consists of, from the inner surface side of the esophagus, a mucosal epithelium (EP), a lamina propria mucosa (LPM), a muscularis mucosa (MM), a submucosal layer (SM), a proper muscular layer, and an adventitia. When the SCC remains in the mucosal epithelium (EP), the SCC is denoted as "EP", and is classified as "Tis". When the SCC reaches the lamina propria mucosa (LPM) below the mucosal epithelium, the SCC is denoted as "LPM", and, in the same manner, when the SCC reaches the muscularis mucosa (MM), the SCC is denoted as "MM", and both are classified as "T1a".

These mucosal epithelium, lamina propria mucosa, and muscularis mucosa correspond to the portion generally referred to as a "mucous membrane". According to a Japanese guideline and a European guideline, it is preferable to apply ER to the esophageal SCC having reached the epithelium (EP)/lamina propria mucosa (LPM), and the muscularis mucosa (MM) by 200 μm or so.

When the SCC has reached the submucosal layer below the lamina propria mucosae, the SCC is denoted as "SM1", "SM2", or "SM3", depending on the depth thereof, and they are all classified as "T1b". The boundaries between the classifications of "SM1", "SM2", and "SM3" are not clear, but can be classified instinctively into three classes of near surface of a submucosal layer, an intermediary portion of the submucosal layer, and a submucosal deep layer.

The guidelines mentioned above do not suggest anything about the applicability of the ER to the SCC classified as T1b having reached a level deeper than T1a. However, there is a report that when the invasion depth of the SCC is T1a (MM and SM1), the probability of the SCC metastasis is less than 10%, so that the ER is considered as the most appropriate initial treatment for T1a (MM and SM1), particularly when the patient is old or weak, based on the high mortality of the esophagectomy and the substantial morbidity. The esophagectomy is usually applied to the cases of T1b (the intermediary portion of the submucosal layer (SM2) or the deep submucosal layer (SM3)), because their risk of metastasis is over 25%. Therefore, the most important task for preoperative diagnosis of the SCC invasion depth is to distinguish T1a (EP and SM1) and T1b (SM2 or SM3).

[About Data Set]

The CNN as an AI system was trained using endoscopic images captured daily in the clinic to which one of the inventors of the present invention belongs. The endoscope systems used included high-resolution or high-definition upper gastrointestinal endoscopes (GIF-XP290N, GIF-Q260J, GIF-RQ260Z, GIF-FQ260Z, GIF-Q240Z, GIF-H290Z, GIF-H290, GIF-HQ290, and GIF-H260Z; manufactured by Olympus Corporation, Tokyo, Japan) and video processors (CV260; manufactured by Olympus Corporation), high-definition magnification gastrointestinal endoscopes (GIF-H290Z, GIF-H290, GIF-HQ290, GIF-H260Z: manufactured by Olympus Corporation) and video processors (EVIS LUCERA CV-260/CLV-260, and EVIS LUCERA ELITE CV-290/CLV-290SL; manufactured by Olympus Medical Systems Corp.), and high-resolution endoscopes (EG-L590ZW, EG-L600ZW, and EG-L600ZW7; manufactured by FUJIFILM Corporation, Tokyo, Japan) and a video endoscope system (LASEREO: manufactured by FUJIFILM Corporation).

The training images were images captured with standard white light imaging, narrow-band imaging (NBI), and blue-laser imaging (BLI), but the images of the patients who met the following exclusion criteria were excluded. The excluded images were those of patients who have severe esophagitis, those of patients with the history chemotherapy, those of patients having their esophagus exposed to radiation, or those with a lesion located adjacently to an ulcer or the scar of an ulcer; low quality image filled with an excessively small amount of air; or those with bleeding, halation, or blurring, those out of focus, or those with mucus.

After the selection, 8,660 non-ME images and 5,678 ME images were collected from pathologically proven superficial esophageal SCC of 804 patients as the training image data set. These images were stored in Joint Photographic Experts Group (JPEG) format, and were pathologically classified into pEP and pLPM, pMM, pSM1, pSM2 and pSM3 cancers, based on the pathological diagnoses of their resected specimens. Under the medical instructor of the Japan Gastroenterological Endoscopy Society, a rectangular frame-like mark was then manually assigned. All of the cancer regions were marked for pEP-pSM1 cancers, and only pSM2 and pSM3 were marked for SM2 and SM3 cancers in a special fashion.

As to a structure enhancement of the endoscope video processor, the narrow-band imaging (NBI) was set to the B-mode level 8, and the level of the blue-laser imaging (BLI) was set to 5 to 6. A black soft hood was attached to the tip of the endoscope so that an appropriate distance was ensured between the tip of the endoscope zoom lens and the surface of the mucous membrane during the magnified observations. The degrees of protrusions and depressions, and the hardness of the cancers were evaluated by performing initial routine examinations with the non-magnification white light imaging, NBI, or BLI.

By magnifying the NBI image, changes in the external appearance of the superficial blood vessel structures, particularly those in the capillary loops in the capillary, were then evaluated. Finally, in order to visualize the spread of the cancer, the lesion was stained with iodine.

[Training/Verification Algorithm]

For the AI-based diagnostic system according to the fourth embodiment, a CNN architecture referred to as Single Shot Multibox Detector (SSD) and the Caffe framework, which were substantially the same as those used in the third embodiment, were used without changing the algorithm.

The training of the model was carried out using stochastic gradient descent at a global learning rate of 0.0001. Each of the images was resized to 300×300 pixels, and the size of the rectangular frame was also changed so that the optimal CNN analysis was to be performed. These values were set through trial and error to ensure that every piece of data has compatibility with SSD.

[Measurement Result and Statistics]

The evaluations of the CNN-based AI system were carried out using independent verification test data of superficial esophageal SCC. Images were collected from patients who received ESD or esophagectomy within a period between January 2017 and April 2018, in the hospital to which one of the inventors of the present invention belongs. After the patients who met the same exclusion criteria as those for the training data set were excluded, 155 patients were selected. Three to six typical images (non-ME and ME) were selected per patient, and diagnoses were made by the AI system.

The trained CNN then generated a diagnose of an EP-SM1 or SM2/SM3 cancer having a continuous number between 0 and 1 which corresponds to the probability of the diagnosis. When it was diagnosed that all regions of the lesion are limited to EP-SM1, the lesion was diagnosed as an EP-SM1 cancer. When it was diagnosed that a part of the lesion has entered the SM2 or SM3 level, the lesion was diagnosed as an SM2/3 cancer. The results of the non-ME, the ME, and the final diagnosis (non-ME+ME) were then analyzed.

In order to compare the correctness of the AI system with that of the physicians, 16 endoscopy specialists were invited from the Japan Gastroenterological Endoscopy Society as the endoscopy specialists. These endoscopy specialists had 9 to 23 years of expertise as physicians, and had experiences of 3000 to 20000 endoscopic examinations. They also made preoperative diagnosis, and performed endoscopic resections of gastrointestinal cancers, on a daily basis. The same verification test data as that provided to the AI system was provided to the endoscopy specialists, and the specialists made diagnoses of EP-SM1 or SM2/SM3 cancer.

Main output indices were diagnosis accuracy, sensitivity, specificity, positive prediction value (PPV), negative prediction value (NPV), and diagnosis time. These values were then compared between the AI system and those of the endoscopy specialists. In order to evaluate variations among the observers in the diagnoses of the invasion depth of the cancers, κ statistic was used. κ value >0.8 represents almost complete match, and κ value=0.8 to 0.6 represents substantial match. κ value=0.6 to 0.4 represents moderate match, and κ value=0.4 to 0.2 represents low match. κ value <0.2 represents slight match. κ value=0 represents accidental match, and κ value <0 indicates non-match. All of these calculations were performed using statistics software EZR.

This survey was carried out under the approval of the Ethical Review Board of the Osaka International Cancer Institute (No. 2017-1710059178), and the Japan Medical Association Ethical Review Board (ID JMA-IIA00283).

In order to examine the validity of the diagnoses of the AI, 405 non-ME images and 509 ME images from 155 patients were selected in total. Table 14 provides a summary of the demographic statistics of the selected patients.

TABLE 14

| Features of patients (n = 155) | |
| --- | --- |
| Sex (male/female) | 128/27 |
| Mean average (age (range)) | 69 (44-90) |
| Features of Lesion (n = 155) | |
| Median tumor size (mm (range)) | 18 (4-95) |
| Position of tumor (Ce/Ut/Mt/Lt/Ae) | 4/25/64/57/5 |
| Macroscopic height (0-I, 0-IIa)/squamous(IIb)/depression (0-IIc) | 32/25/98 |
| Tumor depth (EP-LPM/MM/SM1/SM2-) | 117/10/4/24 |

Ce: cervical esophagus,
Ut: upper thoracic esophagus,
Mt: middle thoracic esophagus,
Lt: lower thoracic esophagus
EP: epithelium,
LPM: lamina propria mucosa,
MM: muscularis mucosa,
SM: submucosal layer The time required for making the diagnosis for all of the images was 29 seconds. As indicated in Table 15, in the final diagnoses of the pEP-SM1 cancers (non-ME+ME), the AI achieved a sensitivity of 90.1%, a degree of specificity of 95.8%, a positive prediction value of 99.2%, a negative prediction value of 63.9%, and an accuracy of 91.0%.

TABLE 15

| | Sensitivity | Specificity | PPV | NPV | Correctness |
| --- | --- | --- | --- | --- | --- |
| Diagnoses by AI | | | | | |
| Final diagnoses | 90.1% (95% CI 83.6-94.6) | 95.8% (95% CI 78.9-99.9) | 99.2% (95% CI 95.4-100) | 63.9% (95% CI 46.2-79.2) | 91.0% (95% CI 85.3-95.0) |
| Non-ME diagnoses | 95.4% (95% CI 90.3-98.3) | 79.2% (95% CI 57.8-92.9) | 96.2% (95% CI 91.3-98.7) | 76.0% (95% CI 54.9-90.6) | 92.9% (95% CI 87.7-96.4) |
| ME diagnoses | 91.6% (95% CI 85.5-95.7) | 79.2% (95% CI 57.8-92.9) | 96.0% (95% CI 90.9-98.7) | 63.3% (95% CI 43.9-80.1) | 89.7% (95% CI 83.8-94.0) |
| Diagnoses by Endoscopy Specialists | | | | | |
| Comprehensive diagnoses | 89.8% (95% CI 86.2-93.4) | 88.3% (95% CI 80.6-95.9) | 97.9% (95% CI 96.5-99.1) | 65.5% (95% CI 58.1-72.8) | 89.6% (95% CI 87.2-91.9) |
| Non-ME diagnosis | 90.6% (95% CI 87.1-94.1) | 87.2% (95% CI 81.4-93.1) | 97.6% (95% CI 96.6-98.6) | 67.2% (95% CI 59.2-75.3) | 90.1% (95% CI 87.7-92.5) |
| ME diagnosis | 91.5% (95% CI 88.4-94.6) | 77.3% (95% CI 68.4-86.3) | 95.8% (95% CI 94.4-97.3) | 66.5% (95% CI 59.3-73.7) | 89.3% (95% CI 87.3-91.2) |

PPV: positive predictive value,
NPV: negative predictive value,
ME: magnification endoscopic examinations In the non-ME diagnoses of the pEP-SM1 cancers, the AI achieved a sensitivity of 95.4%, a degree of specificity of 79.2%, a positive prediction value of 96.2%, a negative prediction value of 76.0%, and an accuracy of 92.9%. In the ME diagnoses of the pSM1 cancers, the AI achieved a sensitivity of 91.6%, a degree of specificity of 79.2%, a positive prediction value of 96.0%, negative prediction value 63.3%, and an accuracy of 89.7%.

In order to examine the performance of the AI in distinguishing the M cancers from the SM cancers, the same validity examination test data, that is, 405 non-ME images and 509 ME images from the 155 patients were selected. The time required for making the diagnoses for all of the images was 29 seconds. In the final diagnoses of the pM cancers, the AI achieved a specificity of 89.0% (95% CI, 82.2% to 93.8%), 92.9% (95% CI, 76.5% to 99.1%), a positive prediction value of 98.3% (95% CI, 48.3% to 79.4%), and an accuracy of 89.7% (95% CI, 83.8% to 94.0%).

In the non-ME diagnoses of the pM cancers, the AI achieved a sensitivity of 93.7% (95% CI, 88.0% to 97.2%), a degree of specificity of 75.0% (95% CI, 55.1% to 89.3%), a positive prediction value of 94.4% (95% CI, 88.9% to 97.7%), a negative prediction value of 72.4% (95% CI, 52.8% to 87.3%), and an accuracy of 90.3% (95% CI, 84.5% to 94.5%). In the diagnoses of the pM cancers with the ME, the AI achieved a sensitivity of 93.7% (95% CI, 88.0% to 97.2%), a degree of specificity 85.7% (95% CI, 67.3% to 96.0%), a positive prediction value of 96.7% (95% CI, 56.6% to 88.5%), and an accuracy of 92.3% (95% CI, 86.9% to 95.9%).

The invasion depths of the SCCs in the same validity test data were diagnosed by the 16 endoscopy specialists (Table 16). The AI achieved, as a whole, a sensitivity of 89.8%, a specificity of 88.3%, a positive prediction value of 97.9%, a negative prediction value of 65.5%, and an accuracy of 89.6%. In subgroup analyses of the endoscopy specialists who have a long-term expertise (16 years or more) and of those who have a short-term expertise (less than 16 years), the diagnosis accuracies were 91.0% and 87.7%, respectively. The degree of match between the observers for the diagnoses was 0.303 (Fleiss' κ coefficient, Z=41.1, p value=0.000). The time required for evaluating the entire verification test data was 115 minutes (within a range between 70 and 180 minutes).

The diagnosis accuracies of the AI system based on the lesion characteristics are indicated in Tables 16 and 17. The correctness of the AI system and the endoscopy specialists include the nature of the lesion, e.g., the depth of cancer infiltration, the form, and the size of the lesion.

TABLE 16

| Invasion depth of cancer | Diagnoses by AI model | | Diagnoses by endoscopy specialists | |
| --- | --- | --- | --- | --- |
| | EP-SM1 | SM2- | EP-SM1 | SM2- |
| pEP/LPM | 94.00% | 6.00% | 93.40% | 6.60% |
| pMM/SMl | 57.10% | 42.90% | 60.30% | 39.70% |
| pSM2 | 4.20% | 95.80% | 11.70% | 88.30% | p: Pathology,
EP: epithelium,
LPM: lamina propria mucosa,
MM: muscularis mucosa,
SM: submucosal layer

TABLE 17

| Features of Cancer | Final diagnosis accuracy by AI | Final diagnosis accuracy by endoscopic specialists |
|---|---|---|
| Protrusion | 81.30% | 77.30% |
| Squamous | 100.00% | 97.50% |
| Depression | 91.80% | 91.60% |
| −10 mm | 83.30% | 89.20% |
| 11-30 mm | 93.30% | 91.10% |
| 31-50 mm | 92.60% | 88.40% |
| 50 mm- | 87.50% | 78.10% |

The non-ME diagnoses made by the AI system exhibited a high performance A large portion of the non-ME images was white light images. The non-ME using white light imaging is a conventional endoscopic imaging approach that is the most common approach available worldwide. The diagnoses of cancer invasion depths using the conventional non-ME are subjective, and are based on the protrusion, the depression, and the hardness of the cancer which may be affected by variations among observers.

Such variations in the diagnoses of the cancer invasion depths with such a conventional non-ME were rooted in its low objectivity, and the low objectivity damaged the reliability and prevented the application of the non-ME as a tool for diagnosing the invasion depth of cancers. However, because the diagnoses made by the AI system according to the fourth embodiment can provide clear diagnoses, objective diagnoses can be provided, and the variability issue can be addressed. By contrast, the diagnoses performance of the ME was disadvantageous in the AI system according to the fourth embodiment. This unpreferable performance is due to the small amount of ME images as the training images. By accumulating a larger training data set for the ME, further improvements can be expected.

As described above, the AI system according to the fourth embodiment exhibited a high performance for diagnoses of the cancer invasion depths of superficial esophageal SCCs, and the accuracy of the final diagnoses was 91.0%, and was comparable to the accuracy of the endoscopy specialists with a long-term expertise.

Fifth Embodiment

Explained now in a fifth embodiment are a diagnostic assistance method, a diagnostic assistance system, a diagnostic assistance program, and a computer-readable recording medium storing therein the diagnostic assistance program for diagnosing a superficial non-ampullary duodenal epithelial tumor (SNADET) by building a diagnostic system using an esophagogastroduodenoscopic (EGD) images, and making the diagnosis based on an EGD image with the CNN.

To begin with, the names of main anatomical sites of the duodenum will be explained with reference to FIG. 16. The duodenum is classified into, from the side closer to the stomach, the bulb, superior part, superior duodenal flexure, descending part, inferior duodenal flexure, horizontal part, ascending part, and jejunum. Although not illustrated, the descending part has two protuberances on the inner side. One of the protuberances is minor duodenal papilla to which the accessory pancreatic duct opens, and the other is the major duodenal papilla (Vater papilla) to which the pancreatic duct and the common bile duct open. The bulb is continuous to the pyloric region (see FIG. 2) of the stomach, and the jejunum is continuous to the cecum in the large bowel via the ileum (not illustrated). The duodenum makes up a part of the small bowel.

[About Data Set]

The CNN as an AI system was trained using EGD images captured in EGD examinations carried out as screening or pre-treatment examinations in the clinic to which one of the inventors of the present invention belongs, in their daily clinical practice. The endoscope systems used included high-resolution or high-definition upper gastrointestinal endoscopes (GIF-H290Z, GIF-H290, GIF-H260Z, and GIF-Q240Z+Olympus Medical Systems, Co., Ltd/Tokyo, Japan).

As the training images, EGD images captured from 87 patients (96 lesions) within a period between August 2016 and November 2018 in the Osaka International Cancer Institute were retroactively considered. A total of 1546 training images were collected from the SNADET lesions of 96 cases that included 31 cases histologically diagnosed as severe dysplasia and 65 cases as adenoma. The pathological diagnoses were made under the supervision of certified clinicians or clinical specialists. Most of the diagnoses were made based on resected specimens, but some were made based on biopsy.

An endoscopy specialist manually assigned a rectangular boundary box to all of the images including an SNADET lesion, and another endoscopy specialist checked the assignment. The endoscopic images having an SNADET lesion were further screened, and images that were unclear due to various reasons, e.g., inclusion of halation, blurring, being out of focus, mucus, food residue, and bleeding after biopsy, were then excluded. Finally, 531 endoscopic images having an SNADET lesion were acquired as a training data set.

In order to evaluate the accuracy of diagnoses made by the built CNN, another data set different from the training data set was also prepared as a test data set. As the test data set, 399 images acquired from 36 cases of lesions (9 severe dysplasia cases, and 27 adenoma cases; among those, 141 were white light images, 61 were indigo-carmine stained images, and 197 were narrow-band images) and 681 normal images (573 white light images and 108 narrow-band images) were prepared.

[Training/Verification Algorithm]

For the AI-based diagnostic system according to the fifth embodiment, a CNN architecture referred to as Single Shot MultiBox Detector (SSD) and the Caffe framework, which were substantially the same as those used in the third embodiment, were used without changing the algorithm. The CNN was trained with stochastic gradient descent at a global learning rate of 0.0001. Each of the images was resized to 300×300 pixels, and the size of the rectangular frame was also changed so that the optimal CNN analysis was to be performed. These values were set through trial and error to ensure that every piece of data has compatibility with SSD.

A fully experienced endoscopy specialist manually assigned a rectangular boundary box to all of the regions representing an SNADET in the training image set, and another endoscopy specialist double-checked each of the images. The CNN was then trained so as to recognize that the region inside a boundary box represented an SNADET region, and the remaining regions were the background.

[Measurement Results and Statistics]

After building the CNN using the training image set, performance of the CNN was evaluated using the test images prepared as the verification data set. To begin with, when the trained CNN detected an SNADET from the input data of a test image, the CNN made a diagnosis (severe dysplasia or adenoma), and displayed a rectangular boundary box with a probability score in the endoscopic image in a manner surrounding a given lesion. The cut-off value of the probability scores was set to 0.4, and, even if the CNN detected a lesion, the CNN determined the lesion to be negative when the probability score was lower than 0.4.

Furthermore, it was determined that the CNN succeeded in detecting an SNADET correctly when the CNN succeeded in assigning a boundary box that overlapped, at least partially, with the boundary box assigned by the endoscopy specialist. When the CNN failed to recognize an SNADET in an image the endoscopy specialist recognized as including an SNADET, it was determined to be false negative. When the CNN diagnosed a non-tumor structure as an SNADET, it was determined to be false positive. The main evaluation items included accuracy, sensitivity, degree of specificity, positive predictive value (PPV), and negative predictive value (NPV). The sensitivity of the CNN was calculated by dividing the number of cases correctly diagnosed as an SNADET by the actual number of SNADETs.

The degree of specificity was calculated by dividing the number of images correctly diagnosed as non-SNADET by the CNN, by the total number of non-SNADET images. The PPN was calculated by dividing the number of images correctly diagnosed as SNADETs by the CNN, by the total image diagnosed as SNADETs by the CNN. The NPV was then calculated by dividing the number of images correctly diagnosed as non-SNADET by the CNN, by the number of all images diagnosed as non-SNADET by the CNN. All of the statistical analyses were done using R software (ver. 3.5.1), and p values less than 0.05 were considered statistically significant.

This test was carried out under the approval of the Ethical Review Board of the Osaka International Cancer Institute (No. 2017-1710059178), and the approval of the Japan Medical Association Ethical Review Board (ID: JMA-IIA00283).

TABLE 18

| Sex | Male | 23 |
|---|---|---|
| | Female | 10 |
| Median age (range) | | 70 (48-90) |
| Median tumor size, mm (range) | | 12 (3-50) |
| Tumor position | bulb | 4 |
| | others | 32 |
| Macroscopic classification | 0-I | 32 |
| | 0-IIa | 26 |
| | 0-IIc | 5 |
| | 0-IIa + IIc | 2 |
| Histopathological classification | Adenoma | 27 |
| | Severe dysplasia | 9 |

Table 18 indicates the features of 33 patients and of 36 cases of the lesions used in the test image set. The 9 lesions (25%) were severe dysplasia, and 27 lesions (75%) were adenoma. The mean tumor size was 12 mm (within a range of 3 mm to 50 mm). The CNN diagnosed 1080 images in total, including images acquired from 36 cases of SNADET lesions (399 images in total), and images of normal duodenum (681 images). The trained CNN detected 94.7% of SNADET lesions (378 images out of 399) on the image basis, and detected 100% on the lesion basis. The CNN detected all of the lesions even though the SNADET lesions included 5 cases of lesions having a size of 5 mm or smaller.

Figure 17A:
FIG. 17A is one example of an endoscopic image of the duodenum.
Figure 17B:
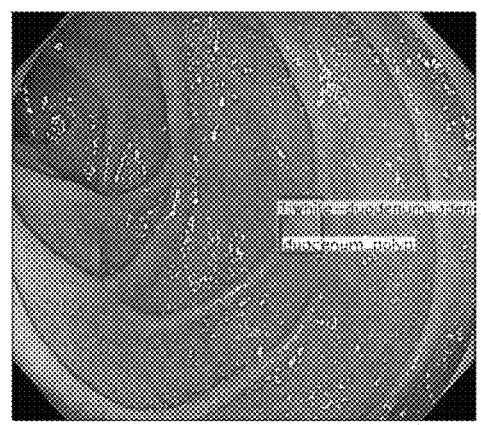
FIG. 17B is a view illustrating an image recognized correspondingly to the part illustrated in FIG. 17A, by the CNN according to a fifth embodiment.

FIG. 17A illustrates an image of a small lesion having a diameter of 3 mm, but the CNN succeeded in detecting such a small lesion not only in a close-up image but also in a relatively distant image, as illustrated in FIG. 17B. The time required for CNN to make the diagnoses of 399 images including SNADETs and 1080 images including normal images were 12 seconds and 31 seconds, respectively. The detailed results of the diagnoses made by the AI in the fifth embodiment are indicated in Table 19. The sensitivity and the degree of specificity of the AI diagnoses were 94.7% (378/399) and 87.4% (596/681), respectively. The positive predictive value (PPV) and the negative predictive value (NPV) were 80.8% and 97.4%, respectively.

TABLE 19

| Sensitivity | 94.7% (378/399) |
|---|---|
| Degree of specificity | 87.4% (595/681) |
| PPV | 80.8% (383/474) |
| NPV | 97.4% (595/611) |

PPV: positive predictive value
NPV: negative predictive value

Figure 18A:
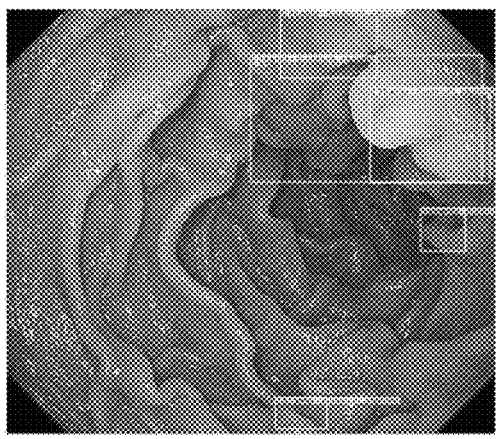
FIG. 18A is an image of normal duodenum folds diagnosed as a false positive by the CNN according to a fifth embodiment.
Figure 18B:
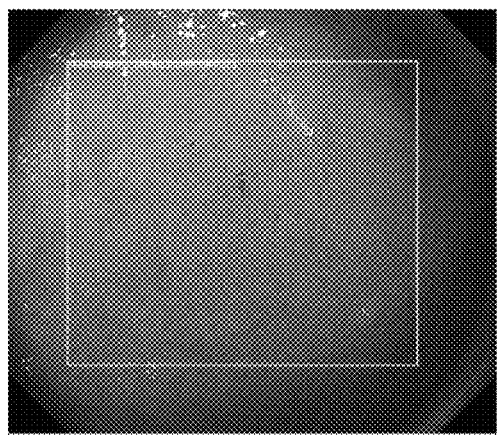
FIG. 18B is an image of normal duodenum mucous membrane diagnosed as a false positive.
Figure 18C:
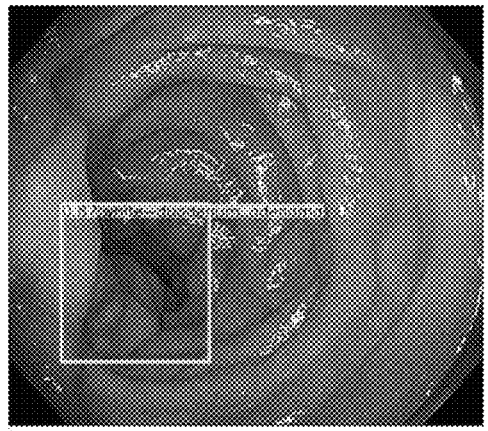
FIG. 18C is an image of ampullary folds of the duodenum, diagnosed as a false positive.
Figure 18D:
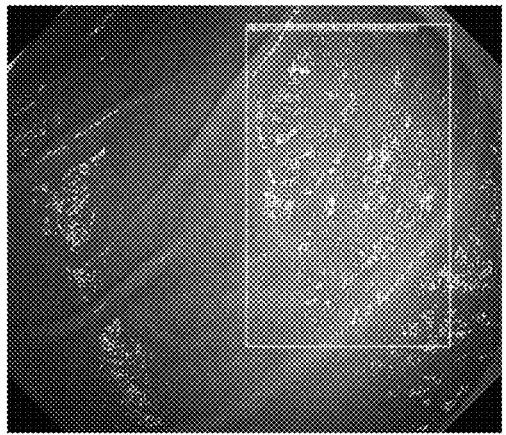
FIG. 18D is an example of a low-quality image with halation, diagnosed as a false positive.

The incidence of false positives was 12.6% (86 images out of 681 normal images). The false positives occurred in folds of the normal duodenum (45 images), mucous membrane of the normal duodenum (23 images), papillary folds of the duodenum (9 images), and low-quality images (for example, due to halation, 9 images). The images of duodenum resulted in false positives are illustrated in FIG. 18. FIG. 18A is an image of the folds of the normal duodenum resulted in a false positive; FIG. 18B is an image of mucous membrane of the normal duodenum resulted likewise in a false positive; FIG. 18C is an image of the papillary folds of the duodenum resulted likewise in a false positive; and FIG. 18D is an example of a low-quality image with halation resulted likewise in a false positive. Most of the erroneous detections of false positives probably resulted from erroneous interpretations of protuberances involved in peristalsis movement as a lesion.

Furthermore, the incidence of false negatives was 5.3% (21 images out of 399 images). A large portion of these false negatives resulted from imaging of the focus located at a distance (see FIG. 19). For example, FIG. 19A is an example of an image recognized as an SNADET by an endoscopy specialist and assigned a rectangular frame but not successfully recognized by the CNN as an SNADET. FIG. 19B is an example of an image recognized as an SNADET by, and assigned a rectangular frame by the endoscopy specialist, and recognized as an SNADET by, and assigned a rectangular frame by the CNN inside the rectangular frame by the endoscopy specialist, but was not determined as an SNADET, because the probability score was 0.24, which was smaller than a cut-off value of 0.4. In this manner, causes of false negatives were mostly based on lesion portions for which the images were captured at a distance, and it was difficult even experienced endoscopy physicians to detect the lesions correctly merely with such images.

Usually, screening of duodenum is done using white light imaging (WLI), and a detailed observation using the narrow-band imaging (NBI) sometimes follows. Therefore, most of WLI images are captured at a greater distance, and most of the NBI images are captured at a shorter distance. The comparisons between the diagnosis results for WLI and of NBI are indicated in Table 20.

TABLE 20

| | AI diagnosis result with WLI | AI diagnosis result with NBI | P value |
|---|---|---|---|
| Sensitivity | 92.9% (131/141) | 98.5% (194/197) | 0.009 |
| Degree of specificity | 89.2% (511/573) | 77.8% (84/108) | 0.001 |

WLI: white light imaging
NBI: narrow-band imaging

According to Table 20, the sensitivity of NBI was significantly higher than that achieved by WLI (p=0.009). By contrast, the degree of specificity of the WLI was significantly higher than that achieved by NBI (P=0.001). In other words, NBI exhibited significantly higher sensitivity and lower degree of specificity for SNADETs, than those exhibited by WLI. Considering the fact that NBI emphasizes surface structures, NBI might contribute to actual improvement in the sensitivity for SNADETs, but there is a possibility that these results become biased, due to some factors such as the conditions of the images or the training data set. Furthermore, while the WLI includes mucous membrane around the lesion portion because the image is captured from a distance, NBI mainly includes the lesion portion. The lack of normal structures in the NBI training data set according to the fifth embodiment may have been the cause of low degree of specificity.

As described above, with the CNN according to the fifth embodiment, all of the 399 images of lesions were verified in 12 seconds, that is, 33 images were analyzed per second. This implies that the SNADET can be detected in real time, in the daily endoscopic diagnoses.

Sixth Embodiment

A diagnostic assistance method for a disease based on an endoscopic image of a digestive organ with use of a CNN according to a sixth embodiment will now be explained with reference to FIG. 20. In the sixth embodiment, a diagnostic assistance method for a disease based on an endoscopic image of a digestive organ with use of a CNN according to any one of the first to the fifth embodiments may be used. At S1, the CNN is trained/verified with a first endoscopic image of a digestive organ, and with at least one final diagnosis result on positivity or negativity to the disease in the digestive organ, a past disease, a severity level, an invasion depth of the disease, and information corresponding to a site where an image is captured, the final diagnosis result being corresponding to the first endoscopic image. When the CNN is intended for diagnosis of a disease related to *H. pylori* in a gastroscopic image, not only the image data representing *H. pylori* positives and *H. pylori* negatives but also *H. pylori* eradicated image data are included.

At S2, the CNN trained/verified at S1 outputs at least one of the probability of the positivity and/or the negativity to the disease in the digestive organ, the probability of the past disease, the severity level of the disease, or the probability corresponding to the site where the image is captured, based on a second endoscopic image of the digestive organ. This second endoscopic image represents a newly observed endoscopic image.

At S1, the first endoscopic image may be associated with the site where the first endoscopic image is captured. The site may include at least one of the pharynx, esophagus, stomach, duodenum, small bowel, and large bowel, and this site may be sectioned into a plurality of sections in at least one of a plurality of digestive organs.

When the first endoscopic image includes a gastroscopic image, it is also possible to include, at S1, not only the positivity or the negativity to the *H. pylori* infection as the disease, but also the presence of *H. pylori* eradication. At least one of the probability of the positive *H. pylori* infection, the probability of the negative *H. pylori* infection being, and the probability of having the *H. pylori* eradicated may be output at S2.

When the first endoscopic image includes a colonoscopic image, the terminal ileum, the cecum, the ascending colon, the transverse colon, the descending colon, the sigmoid colon, the rectum, and the anus may be included as sections at S1. At S2, as the section of the large bowel in the second endoscopic image, a probability corresponding to at least one of the terminal ileum, the cecum, the ascending colon, the transverse colon, the descending colon, the sigmoid colon, the rectum, and the anus may be output, or a probability corresponding to at least one of the terminal ileum, the cecum, the ascending colon and transverse colon, the descending colon and sigmoid colon, the rectum, and the anus may be output. Furthermore, a probability corresponding to at least one of the terminal ileum, the right colon including the cecum-ascending colon-transverse colon, and the left colon including the descending colon-sigmoid colon-rectum, and the anus may also be output.

Furthermore, at S2, the second endoscopic image may be at least one of an image captured by an endoscope, an image transmitted over a communication network, an image provided by a remote control system or a cloud system, an image recorded in a computer-readable recording medium, and a video.

Seventh Embodiment

A diagnostic assistance system for a disease based on an endoscopic image of a digestive organ, a diagnostic assistance program using an endoscopic image of a digestive organ, and a computer-readable recording medium according to a seventh embodiment will now be explained with reference to FIG. 21. In the seventh embodiment, the diagnostic assistance system for a disease based on an endoscopic image of a digestive organ explained in the fourth and the fifth embodiments may be used.

This diagnostic assistance system 1 for a disease based on an endoscopic image of a digestive organ includes an endoscopic image input unit 10, a computer 20 incorporated with a CNN, and an output unit 30. The computer 20 includes: a first storage area 21 that stores therein a first endoscopic image of a digestive organ; a second storage area 22 that stores therein at least one final diagnosis result on positivity or negativity to the disease in the digestive organ, a past disease, a severity level, and information corresponding to a site where an image is captured, the final diagnosis result being corresponding to the first endoscopic image; and a third storage area 23 storing therein a CNN program. The CNN program stored in the third storage area 23 is trained/verified based on the first endoscopic image stored in the first storage area 21, and on the final diagnosis result stored in the second storage area 22, and outputs at least one of a probability of the positivity and/or the negativity to the disease in the digestive organ, a probability of the past disease, a severity level of the disease, or a probability corresponding to the site where the image is captured, to the output unit 30, for the second endoscopic image, based on a second endoscopic image of the digestive organ input from the endoscopic image input unit 10.

The first endoscopic image stored in the first storage area 21 may be associated with a site where the first endoscopic image is captured. The site may include at least one of the pharynx, esophagus, stomach, duodenum, small bowel, and large bowel, and the site may be sectioned into a plurality of sections, in at least one of a plurality of digestive organs.

When the first endoscopic image stored in the first storage area 21 includes a gastroscopic image, the final diagnosis result stored in the second storage area 22 may include not only the positivity or negativity to the *H. pylori* infection, but also the presence of the *H. pylori* eradication. For the second endoscopic image stored in the third storage area, the output unit 30 may output at least one of a probability of the positive *H. pylori* infection, a probability of the negative *H. pylori* infection, and a probability of the eradicated *H. pylori*.

When the first endoscopic image stored in the first storage area 21 includes a colonoscopic image, the sections of the final diagnosis results stored in the second storage area 22 may include the terminal ileum, the cecum, the ascending colon, the transverse colon, the descending colon, the sigmoid colon, the rectum, and the anus. For the sections of the large bowel in the second endoscopic image stored in the third storage area, the output unit 30 may output a probability corresponding to at least one of the terminal ileum, the cecum, the ascending colon, the transverse colon, the descending colon, the sigmoid colon, the rectum, and the anus, for example. The output unit 30 may also output the probability corresponding to at least one of the terminal ileum, the cecum, the ascending colon and transverse colon, the descending colon and sigmoid colon, the rectum, and the anus. Alternatively, the output unit 30 may also output a probability corresponding to at least one of the terminal ileum, the right colon including the cecum-ascending colon-transverse colon, and the left colon including a descending colon-sigmoid colon-rectum, and the anus.

Furthermore, the second endoscopic image stored in the third storage area may be at least one of an image captured by an endoscope, an image transmitted over a communication network, an image provided by a remote control system or a cloud system, an image recorded in a computer-readable recording medium, and a video.

The diagnostic assistance system for a disease based on an endoscopic image of a digestive organ according to the seventh embodiment is provided with a diagnostic assistance program using an endoscopic image of a digestive organ, the diagnostic assistance program being a computer program for causing a computer to operate as the units. Furthermore, the diagnostic assistance program using an endoscopic image of a digestive organ may be stored in a computer-readable recording medium.

REFERENCE SIGNS LIST

10 endoscopic image input unit
20 computer
21 first storage area
22 second storage area
23 third storage area
30 output unit

The invention claimed is:

1. A diagnostic assistance method for a disease based on an endoscopic image of a digestive organ with use of a convolutional neural network, the diagnostic assistance method comprising:
training the convolutional neural network using:
a first endoscopic image of the digestive organ; and
a final diagnosis result comprising at least one of: positivity or negativity to the disease in the digestive organ, a past disease, a severity level, an invasion depth of the disease, and information corresponding to a site where an image is captured,
wherein the final diagnosis result corresponds to the first endoscopic image,
wherein the trained convolutional neural network outputs, based on a second endoscopic image of the digestive organ, at least one of: a probability of the positivity and/or the negativity to the disease in the digestive organ, a probability of the past disease, a severity level of the disease, an invasion depth of the disease, and a probability corresponding to the site where the image is captured,
wherein the convolutional neural network is trained by comparing a degree of overlap between a disease-positive region displayed as the final diagnosis result in the second endoscopic image with a disease-positive region in the first endoscopic image.

2. The diagnostic assistance method for a disease based on an endoscopic image of a digestive organ with use of a convolutional neural network according to claim 1, wherein the first endoscopic image is associated with a site of a digestive organ where the image is captured.

3. The diagnostic assistance method for a disease based on an endoscopic image of a digestive organ with use of a convolutional neural network according to claim 2, wherein the site of the digestive organ includes at least one of pharynx, esophagus, stomach, duodenum, small bowel, and large bowel.

4. The diagnostic assistance method for a disease based on an endoscopic image of a digestive organ with use of a convolutional neural network according to claim 3, wherein
the site of the digestive organ is the stomach,
the final diagnosis result includes at least one of positive *H. pylori* infection, negative *H. pylori* infection, and *H. pylori* eradicated, and
the convolutional neural network outputs at least one of: a probability of the positive *H. pylori* infection, a probability of the negative *H. pylori* infection, and a probability of the *H. pylori* eradicated.

5. The diagnostic assistance method for a disease based on an endoscopic image of a digestive organ with use of a convolutional neural network according to claim 3, wherein
the site of the digestive organ is the small bowel,
the endoscopic image is a wireless-capsule endoscopic image, and
the disease is at least one of erosion and ulcer.

6. The diagnostic assistance method for a disease based on an endoscopic image of a digestive organ with use of a convolutional neural network according to claim 3, wherein
the site of the digestive organ is the duodenum,
the endoscopic image is an esophagogastroduodenoscopic image of the duodenum, and
the disease is a superficial non-ampullary duodenal epithelial tumor.

7. The diagnostic assistance method for a disease based on an endoscopic image of a digestive organ with use of a convolutional neural network according to claim 3, wherein the site of the digestive organ is sectioned into a plurality of sections in at least one of the pharynx, the esophagus, the stomach, the duodenum, and the large bowel.

8. The diagnostic assistance method for a disease based on an endoscopic image of a digestive organ with use of a convolutional neural network according to claim 7, wherein
the site of the digestive organ is the large bowel,
the sections include at least one of terminal ileum, cecum, ascending colon, transverse colon, descending colon, sigmoid colon, rectum and anus, and
the convolutional neural network outputs a probability corresponding to whether at least one of the terminal ileum, the cecum, the ascending colon, the transverse colon, the descending colon, the sigmoid colon, the rectum, and the anus is a section where the second endoscopic image is captured.

9. The diagnostic assistance method for a disease based on an endoscopic image of a digestive organ with use of a convolutional neural network according to claim 7, wherein
the site of the digestive organ is the large bowel,
the sections include terminal ileum, cecum, ascending colon and transverse colon, descending colon and sigmoid colon, rectum and anus, and
the convolutional neural network outputs a probability corresponding to whether at least one of the terminal ileum, the cecum, the ascending colon and transverse colon, the descending colon and sigmoid colon, the rectum and anus is a section where the second endoscopic image is captured.

10. The diagnostic assistance method for a disease based on an endoscopic image of a digestive organ with use of a convolutional neural network according to claim 7, wherein
The site of the digestive organ is the large bowel,
the sections include terminal ileum, right colon including cecum-ascending colon-transverse colon, and left colon including descending colon-sigmoid colon-rectum, and anus, and
the convolutional neural network outputs a probability corresponding to whether at least one of the terminal ileum, the right colon including the cecum-ascending colon-transverse colon, and the left colon including descending colon-sigmoid colon-rectum, and anus is a section where the second endoscopic image is captured.

11. The diagnostic assistance method for a disease based on an endoscopic image of a digestive organ with use of a convolutional neural network according to claim 1, wherein
the second endoscopic image further includes a probability score generated by the trained convolutional neural network.

12. The diagnostic assistance method for a disease based on an endoscopic image of a digestive organ with use of a convolutional neural network according to claim 1, wherein the disease-positive region in the second endoscopic image and the disease-positive region in the first endoscopic image are each bounded by at least one rectangular bounding box, and the degree of overlap is determined based on how much the rectangular bounding boxes overlap.

13. The diagnostic assistance method for a disease based on an endoscopic image of a digestive organ with use of a convolutional neural network according to claim 12, wherein
(1) when the degree of overlap is 80% or more, or
(2) when a plurality of disease-positive regions are identified in at least one of the first or the second endoscopic image are identified and the degree of overlap between one of the plurality of disease-positive regions is 80% or more,
the diagnosis made by the trained convolutional neural network is determined to be correct.

14. The diagnostic assistance method for a disease based on an endoscopic image of a digestive organ with use of a convolutional neural network according to claim 3, wherein
the site of the digestive organ is the esophagus,
the endoscopic image is a non-magnification endoscopic image or a magnification endoscopic image, and
the disease is a squamous cell carcinoma and the trained convolutional neural network outputs the invasion depth of the squamous cell carcinoma.

15. The diagnostic assistance method for a disease based on an endoscopic image of a digestive organ with use of a convolutional neural network according to claim 14, wherein the final diagnosis result further comprises a determination that the invasion depth of the squamous cell carcinoma is at least one of: a mucosal epithelium-lamina propria mucosa, a muscularis mucosa, a section near a surface of a submucosal layer, and a level deeper than an intermediary portion of the submucosal layer.

16. The diagnostic assistance method for a disease based on an endoscopic image of a digestive organ with use of a convolutional neural network according to claim 1, wherein the convolutional neural network is combined with three dimensional information from an X-ray computer tomographic imaging apparatus, an ultrasound computer tomographic imaging apparatus, or a magnetic resonance imaging diagnosis apparatus.

17. The diagnostic assistance method for a disease based on an endoscopic image of a digestive organ with use of a convolutional neural network according to claim 1, wherein the second endoscopic image is at least one of an image captured by an endoscope, an image transmitted over a communication network, an image provided by a remote control system or a cloud system, an image recorded in a computer-readable recording medium, and a video.

18. A non-transitory computer-readable storage medium containing instructions which, when executed by a processor, cause the processor to carry out the diagnostic assistance method for a disease based on an endoscopic image of a digestive organ with use of a convolutional neural network according to claim 1.

19. A diagnostic assistance system for a disease based on an endoscopic image of a digestive organ, the diagnostic assistance system comprising an endoscopic image input unit; an output unit; and a computer incorporated with use of a convolutional neural network, wherein
the computer includes:
a first storage area that stores therein first endoscopic images of a digestive organ;
a second storage area that stores therein a final diagnosis result comprising at least one of: positivity or negativity to the disease in the digestive organ, a past disease, a severity level, an invasion depth of the disease, and information corresponding to a site where an image is captured, wherein the final diagnosis result corresponds to the first endoscopic image; and
a third storage area that stores therein instructions for causing a processor to execute the convolutional neural network, wherein
the convolutional neural network:
is trained based on the first endoscopic image stored in the first storage unit, and the final diagnosis result stored in the second storage area, and
outputs, based on a second endoscopic image obtained from the endoscopic image input unit, at least one of: a probability of the positivity and/or the negativity to the disease in the digestive organ, a probability of the past disease, a severity level of the disease, an invasion depth of the disease, and a probability corresponding to the site where the image is captured, for the second endoscopic image, to the output unit,
wherein the convolutional neural network is trained by comparing a degree of overlap between a disease-positive region displayed as the final diagnosis result in the second endoscopic image with a disease-positive region in the first endoscopic image.

20. The diagnostic assistance system for a disease based on an endoscopic image of a digestive organ according to claim 19, wherein the first endoscopic image is associated with a site where the image is captured.

21. The diagnostic assistance system for a disease based on an endoscopic image of a digestive organ according to claim 20, wherein the site of the digestive organ includes at least one of pharynx, esophagus, stomach, duodenum, small bowel, and large bowel.

22. The diagnostic assistance system for a disease based on an endoscopic image of a digestive organ according to claim 21, wherein
the site of the digestive organ is the stomach, and
the convolutional neural network outputs at least one of: a probability of positive *H. pylori* infection, a probability of negative *H. pylori* infection, and a probability of *H. pylori* eradicated based on the second endoscopic image.

23. The diagnostic assistance system for a disease based on an endoscopic image of a digestive organ with use of a convolutional neural network according to claim 21, wherein
the site of the digestive organ is the small bowel, and
the trained convolutional neural network outputs a probability corresponding to at least one of erosion and ulcer as the disease based on the second endoscopic image.

24. The diagnostic assistance system for a disease based on an endoscopic image of a digestive organ with use of a convolutional neural network according to claim 21, wherein
the site of the digestive organ is the duodenum, and
the trained convolutional neural network outputs a probability corresponding to a superficial non-ampullary duodenal epithelial tumor as the disease based on the second endoscopic image.

25. The diagnostic assistance system for a disease based on an endoscopic image of a digestive organ according to claim 21, wherein the site of the digestive organ is sectioned into a plurality of sections, in at least one of the pharynx, the esophagus, the stomach, the duodenum, the small bowel, and the large bowel.

26. The diagnostic assistance system for a disease based on an endoscopic image of a digestive organ according to claim 25, wherein
the site of the digestive organ is the large bowel,
the sections include at least one of terminal ileum, cecum, ascending colon, transverse colon, descending colon, sigmoid colon, rectum, and anus, and
the convolutional neural network outputs a probability corresponding to whether at least one of the terminal ileum, the cecum, the ascending colon, the transverse colon, the descending colon, the sigmoid colon, the rectum, and the anus is a section where the second endoscopic image is captured.

27. The diagnostic assistance system for a disease based on an endoscopic image of a digestive organ according to claim 25, wherein
the site of the digestive organ is the large bowel,
the sections include at least one of terminal ileum, cecum, ascending colon, transverse colon, descending colon, sigmoid colon, rectum, and anus, and
the convolutional neural network outputs a probability corresponding to whether at least one of the terminal ileum, the cecum, the ascending colon and transverse colon, the descending colon and sigmoid colon, the rectum and anus is a section where the second endoscopic image is captured.

28. The diagnostic assistance system for a disease based on an endoscopic image of a digestive organ according to claim 25, wherein
the site of the digestive organ is the large bowel, and
the trained convolutional neural network outputs a probability corresponding to whether at least one of sections of the terminal ileum, the right colon including the cecum-ascending colon-transverse colon, and the left colon including descending colon-sigmoid colon-rectum and anus is a section where the second endoscopic image is captured.

29. The diagnostic assistance system for a disease based on an endoscopic image of a digestive organ according to claim 19, wherein the convolutional neural network is combined with three dimensional information from an X-ray computer tomographic imaging apparatus, an ultrasound computer tomographic imaging apparatus, or a magnetic resonance imaging diagnosis apparatus.

30. The diagnostic assistance system for a disease based on an endoscopic image of a digestive organ according to claim 19, wherein the second endoscopic image is at least one of an image captured by an endoscope, an image transmitted over a communication network, an image provided by a remote control system or a cloud system, an image recorded in a computer-readable recording medium, and a video.

31. A non-transitory computer-readable storage medium containing instructions which, when executed by a processor, cause the processor to function as part of the diagnostic assistance system for a disease based on an endoscopic image of a digestive organ according to claim 19.

* * * * *